US012609187B2

(12) United States Patent
Alsumidaie et al.

(10) Patent No.: US 12,609,187 B2
(45) Date of Patent: Apr. 21, 2026

(54) DATA TRANSFORMATION SYSTEM FOR CLINICAL BUDGETS

(71) Applicant: ANNEX IP, LLC, Miami Beach, FL (US)

(72) Inventors: Moe Alsumidaie, Miami Beach, FL (US); Krishma Shah, Mumbai (IN); Jonathan Napitupulu, Depok (ID)

(73) Assignee: Annex IP, LLC, Miami Beach, FL (US)

( * ) Notice: Subject to any disclaimer, the term of this patent is extended or adjusted under 35 U.S.C. 154(b) by 0 days.

(21) Appl. No.: 19/357,168

(22) Filed: Oct. 14, 2025

(65) Prior Publication Data

US 2026/0105999 A1      Apr. 16, 2026

Related U.S. Application Data

(60) Provisional application No. 63/706,817, filed on Oct. 14, 2024.

(51) Int. Cl.
G06Q 10/10        (2023.01)
G16H 10/20        (2018.01)
G16H 10/60        (2018.01)

(52) U.S. Cl.
CPC .................................. G16H 10/20 (2018.01)

(58) Field of Classification Search
CPC .................................................... G16H 10/20
See application file for complete search history.

(56) References Cited

U.S. PATENT DOCUMENTS

2021/0304879 A1* 9/2021 Morris .................. G16H 50/20
2024/0265399 A1* 8/2024 Qasim ................... G06Q 40/02

* cited by examiner

*Primary Examiner* — Maroun P Kanaan
(74) *Attorney, Agent, or Firm* — Anton J. Hopen; Trenam Law

(57)        ABSTRACT

A computer-implemented method for reconciling clinical trial budgets. The method receives procedural items from a sponsor budget source, a Medicare Coverage Analysis source, and a site charge master source; normalizes procedure text; generates unit-length vector embeddings for each item; and constructs an approximate nearest-neighbor index over site embeddings. For each sponsor item the method retrieves candidate site items by cosine similarity and computes a composite match score that combines code equality, textual similarity, numeric price proximity, and billing consistency with code-dominant weighting. One-to-one matches are selected by maximum-weight bipartite matching. Matched pairs are aligned to Medicare Coverage Analysis items with code-family gating, and a rule engine sets a selected cost value and a resolved billing category subject to contract caps. Unmatched items are flagged with candidate explanations. The method writes per-item audit records and returns a machine-readable payload through an application programming interface.

20 Claims, 3 Drawing Sheets

10

DATA TRANSFORMATION SYSTEM FOR CLINICAL BUDGETS

PRIORITY INFORMATION

This nonprovisional application is a continuation of and claims priority to Provisional Application No. 63/706,817, entitled "Data Transformation System for Clinical Budgets," filed Oct. 14, 2024.

BACKGROUND OF THE INVENTION

1. Field of the Invention

The described embodiments relate generally to data processing systems and methods for automating the reconciliation of clinical trial budgets, including the transformation and comparison of procedural data across multiple sources such as sponsor budgets, Medicare Coverage Analyses, and site charge masters.

2. Brief Description of the Related Art

Clinical trial budgets are essential financial frameworks that ensure the effective execution of clinical studies. These budgets encapsulate the costs associated with patient care, medical procedures, administrative management, and adherence to regulatory standards. For studies to remain viable, it is imperative that budgets accurately reflect the expected financial obligations and provide a clear path for negotiation between key stakeholders such as clinical sites, sponsors, and regulatory bodies like Medicare. However, the process of budget reconciliation in clinical trials is inherently complex, fraught with manual data handling, procedural inconsistencies, and inefficiencies. Understanding these challenges and the core elements of clinical trial budgeting is essential for developing an automated solution to streamline the process.

At the most basic level, a clinical trial budget is a financial plan that outlines the costs of running a study. These costs are not uniform across all studies but instead depend on numerous factors, including the type of trial, the number of participating patients, the duration of the study, and the location and capabilities of the clinical sites. Each site participating in the trial will have its own specific costs, which need to be reconciled with the sponsor's budget and often a Medicare Coverage Analysis (MCA). The MCA serves as a critical financial analysis tool, identifying which costs can be billed to Medicare and which are considered research-related expenses that should be covered by the sponsor.

At the heart of every clinical trial budget are procedural costs. These costs include charges for specific medical procedures, diagnostic tests, and imaging studies required by the study protocol. Each of these procedures is typically associated with a Current Procedural Terminology (CPT) code, a standardized medical code set used for billing purposes. CPT codes ensure that medical services are uniformly billed and reimbursed across different healthcare providers. In clinical trials, these codes are essential for aligning research-related procedures with standard-of-care (SOC) procedures that a patient would normally undergo outside the context of the trial. SOC procedures are typically covered by insurance or Medicare, while research-specific procedures are billed to the trial sponsor.

However, the challenge in reconciling these procedural costs lies in the varying terminologies and procedural codes used across different sources, such as the sponsor's budget, the MCA, and the clinical site's charge master. The charge master is an institution-specific database of services and their associated costs, which hospitals and clinics use for billing purposes. This system ensures that procedural costs reflect the institution's pricing for medical services, which can vary significantly between locations. A key issue arises when similar but not identical procedures are described differently across these sources. For instance, a chest X-ray might be listed under slightly different procedural codes in the sponsor's budget and the MCA. These inconsistencies lead to discrepancies that require manual reconciliation, which is time-consuming and prone to errors.

Personnel costs represent another significant component of clinical trial budgets. These costs include the salaries and wages of all personnel involved in the trial, from the principal investigator (PI) to study coordinators, data managers, and clinical research associates. Personnel effort is often calculated using Full-Time Equivalent (FTE) measures, which estimate the proportion of a full-time employee's work that will be devoted to the trial. Alternatively, personnel costs can be expressed as per-patient fees, where staff time is estimated based on the number of patients enrolled in the study and the number of visits or procedures required per patient. Personnel costs can vary widely depending on the complexity of the study, the experience level of the personnel, and the location of the clinical site. For example, clinical research coordinators at major academic medical centers on the East and West coasts may command significantly higher salaries than those at smaller community hospitals.

In addition to personnel costs and procedural fees, clinical trial budgets must account for various administrative and overhead expenses. These include costs associated with study start-up, Institutional Review Board (IRB) submissions, pharmacy services, data management, and regulatory compliance. Start-up fees, in particular, can be substantial, as they cover the time and effort required to initiate the trial at each site, including contract negotiations, site training, and regulatory approvals. Ongoing administrative costs such as IRB renewals, monitoring visits, and data entry are also necessary to ensure the trial's compliance with regulatory standards and the accuracy of its data. These costs are often charged as flat fees, though they can also be calculated based on the time and effort required for specific tasks.

A crucial aspect of clinical trial budgets is the differentiation between research-related procedures and those classified as standard of care. Standard of care procedures are those that a patient would typically receive as part of their routine medical treatment, regardless of their participation in the trial. These procedures are usually billed to the patient's insurance or Medicare. Research-related procedures, on the other hand, are conducted solely for the purposes of the study and are billed to the sponsor. Differentiating between these two types of procedures is a significant challenge in clinical trial budgeting, as many procedures can have both research and standard of care components. For instance, a blood test that is performed as part of the patient's routine medical care may also be used to collect data for the trial. In such cases, only the research-specific portion of the procedure should be billed to the sponsor, while the standard of care portion should be billed to insurance. Accurately allocating these costs requires a detailed understanding of the study protocol and the ability to parse the procedural codes and descriptions provided by the sponsor and clinical sites.

One of the most significant inefficiencies in clinical trial budget reconciliation is the reliance on manual processes.

Historically, budget negotiations have involved extensive cross-referencing of procedural codes, cost estimates, and administrative fees between the sponsor's budget, the MCA, and the clinical site's charge master. This process is not only labor-intensive but also prone to errors, especially when discrepancies arise in the procedural codes or descriptions used by different stakeholders. For example, a procedure that is listed as "Chest X-ray, 2 views" in the sponsor's budget may be described as "Radiograph of the chest" in the MCA and as "X-ray, chest 2 views" in the site's charge master. While these procedures may be essentially identical, the variations in terminology can lead to mismatches that require manual reconciliation. Moreover, when the procedural codes do not align perfectly-such as when one source uses CPT code 71020 and another uses 71010, which are closely related but distinct-additional manual review is necessary to ensure that the correct procedure is billed.

These manual reconciliation processes introduce delays into the clinical trial budget negotiation process, as each discrepancy must be reviewed and resolved before the final budget can be approved. In large, multi-site trials, this process can be particularly cumbersome, as each site's budget must be reconciled individually, and the potential for discrepancies increases with the number of sites involved. Moreover, the reliance on manual processes increases the risk of errors, which can lead to billing inaccuracies, disputes between the sponsor and the site, and delays in trial execution.

Another challenge in clinical trial budgeting is the variability in pricing for procedures and services across different clinical sites. While the MCA provides a standardized analysis of which costs can be billed to Medicare, the actual costs of procedures can vary significantly between institutions. For example, the cost of a laboratory test or imaging study at a large academic medical center may be much higher than the same procedure at a smaller community hospital. This variability in pricing complicates the budget negotiation process, as sponsors must balance the need to fairly compensate all participating sites while also controlling overall trial costs. In some cases, sponsors may negotiate a fixed per-patient fee for certain procedures, regardless of the actual cost at each site. However, this approach can lead to disparities in reimbursement, with some sites being overcompensated and others undercompensated for the same procedures.

Clinical trial budgets are complex financial frameworks that must account for a wide range of costs, including personnel salaries, procedural fees, and administrative expenses. The process of reconciling these budgets between sponsors, MCAs, and clinical sites is fraught with inefficiencies, due primarily to the reliance on manual data handling and the variability in procedural codes and pricing across different sources. There is a long-felt, but unfulfilled need to automate the budget reconciliation process and streamline the negotiation process, reduce errors, and ensure that budgets accurately reflect the financial realities of clinical trials. Such automation holds the potential to significantly improve the efficiency and accuracy of clinical trial budgeting, ultimately reducing the time and cost required to bring new medical interventions to market.

BRIEF SUMMARY OF THE INVENTION

This invention provides a computer-implemented method that runs on one or more processors to automatically reconcile clinical trial budgets. At a high level, the system ingests three coordinated sources of budgetary and procedural information, transforms the data into machine-processable vectors, retrieves likely matches with sublinear search, computes a composite similarity score that favors exact code agreement, enforces a one-to-one pairing across sources with graph matching, resolves costs and billing categories under policy rules, and produces both a reconciled budget and an audit trail as a machine-readable payload. The same runtime captures unmatched items, proposes data-driven remedies, and learns from operator feedback for improved future performance.

Data ingestion with defined fields. The method begins by receiving structured procedural items from each of three sources: a sponsor budget source, a Medicare Coverage Analysis source, and a site charge master source. Each received item includes a procedure name, a standardized procedure code such as a CPT code, a cost value, and a billing category. These are the exact fields used downstream for normalization, embedding, matching, scoring, policy resolution, and auditing. The ingestion stage preserves every item as a record in memory with those four fields so that later steps can reference "the received plurality of procedural items."

Normalization for text and codes. Before any modeling, the system normalizes procedure names by tokenizing the text, lowercasing, removing punctuation, and expanding abbreviations by consulting a stored synonym dictionary. In the same pass, the method maps procedure codes to canonical code families, so related codes can be compared consistently. This normalization produces the canonical textual and coding forms used when the model generates embeddings and when policy rules evaluate billing categories.

Learned embeddings with numeric features. For each procedural item, the system generates a fixed-length vector embedding that encodes both the normalized procedure name and the item's numerical attributes. A trained text-embedding function converts the normalized text into a dense vector. In one implementation the numeric attributes such as cost value and optional frequency are projected and fused into the text vector. Each resulting vector is normalized to unit length so that cosine similarity equals the inner product during retrieval and scoring.

Sublinear candidate search with a graph index. To avoid quadratic comparisons, the method constructs in memory an approximate nearest neighbor index over the vectors for items from the site charge master source. In one embodiment the index is a graph-based navigable small-world structure with configuration parameters that bound search fan-out and deliver sublinear retrieval. The index supports online queries and is designed to accept incremental insertions as site catalogs change.

Querying site candidates by cosine similarity. With the index built, the system iterates for each item from the sponsor budget source. It queries the index to retrieve a ranked set of candidate site items ordered by cosine similarity between the corresponding unit-length vectors. A fixed top-k candidate list is returned per sponsor item, and subsequent scoring is computed only for those returned candidates in order to bound runtime.

Composite match scoring with calibrated acceptance. For each candidate pair, the system computes a composite match score that includes four components: (1) a code-match indicator that equals 1 when the standardized procedure codes are exactly equal and equals 0 otherwise; (2) a cosine similarity term taken from the embedding vectors; (3) a numeric similarity term that decays exponentially with the absolute difference between cost values divided by a tunable scale parameter; and (4) a billing-consistency term derived from the pair's billing categories.

Each term is weighted according to a stored configuration, and the code-match weight is configured to dominate when codes are equal. The method determines that a candidate pair satisfies a similarity threshold when the composite match score meets or exceeds a calibrated threshold. That threshold is calibrated offline against a held-out validation set of historical budgets to achieve target true-positive and false-positive rates, and the chosen value is stored with model metadata for consistent runtime behavior.

One-to-one assignment by maximum-weight matching. After pruning to candidate edges that pass the threshold, the method forms a weighted bipartite graph whose left nodes are sponsor items and whose right nodes are site items. Edges exist only for pairs that met the threshold, and edge weights equal the composite match scores. The system then selects a one-to-one assignment by computing a maximum-weight matching on this graph. In one embodiment the selection is computed by the Hungarian algorithm executed over a dense score matrix derived from the edge weights. This enforces exclusivity and prevents the same site item from being matched to multiple sponsor items.

Alignment to Medicare Coverage Analysis and code-family gating. For each matched sponsor-site pair, the method seeks a corresponding Medicare Coverage Analysis item either by exact standardized procedure code equality or by reapplying the same embedding and scoring steps with Medicare Coverage Analysis as the comparison dataset. When a Medicare Coverage Analysis code equals the sponsor code or the site code, the method adjusts the composite match score with a predetermined code-match weight. If a Medicare Coverage Analysis item does not share a code family with either the sponsor or site code, its influence is gated out so that it does not boost the composite score.

Policy resolution and reconciled-budget data structure. With cross-source alignment established, the method updates a reconciled budget data structure in memory. For each matched set of items across sources, the structure stores a selected cost value determined as the maximum permitted value under a policy rule set that enforces Medicare Coverage Analysis allowances and contract caps. The structure also stores a resolved billing category chosen by a rule engine, plus provenance fields that identify which source contributed the selected cost. In one configuration the rule engine selects the site cost value when the billing category is research billable and selects the Medicare Coverage Analysis allowed amount when the billing category is standard of care, subject to contract caps, and records any cap enforcement in the audit record for traceability.

Unmatched items and permutation-based re-tokenization. Any sponsor budget item that remains unmatched after maximum-weight matching undergoes a permutation-based re-tokenization pass that reorders tokens and expands abbreviations to create alternate normalized texts. The system re-embeds and re-queries those variants against the index. If still unresolved, the item is flagged and the system stores the top candidate explanations and scores to support efficient manual review.

Audit trail with vector fingerprints and determinism. For each processed item the method writes an audit record that includes a vector fingerprint for the unit-length embedding, the full candidate list, the composite match score components and weights, the match or flag outcome, and the rule rationale applied during cost and billing resolution. To ensure reproducibility and tamper resistance, the system takes an immutable ingestion snapshot at the moment the three sources are received, computes a cryptographic hash over the snapshot, and creates a deterministic run identifier from the snapshot hash combined with versions of the model and configuration artifacts. These identifiers are stored in the audit record and later used by a replay utility to verify numerical equivalence within tolerance.

Machine-readable output via API. At completion, the method transmits the reconciled budget data structure and the audit records as a machine-readable payload through an application programming interface to an external budget management system. In one embodiment the payload is a JSON document that includes, for each reconciled item, fields for the resolved procedure name, resolved standardized procedure code, resolved billing category, selected cost value, the contributing sources, and a reference to the audit record. Flagged items are emitted with their top candidate explanations and scores. In some embodiments, in addition to a JSON payload, the system emits an Excel workbook conforming to a site- or sponsor-specific template. A mapping table associates resolved fields (e.g., standardized procedure code, selected cost value, resolved billing category, provenance flags) to absolute cell addresses or named ranges per worksheet, enabling deterministic placement and preservation of sponsor formatting. The export preserves formulas and conditional formatting in unaffected ranges and writes a manifest sheet listing the reconciliation identifier, snapshot identifier, and model/policy versions used to render the workbook.

Training, learning, and model packaging. The text-embedding function described above is trained by contrastive learning on labeled matching and non-matching pairs constructed from historical clinical trial budgets. The training loop performs hard negative mining by nearest-neighbor retrieval against interim checkpoints so that the model learns to distinguish look-alike terms. The resulting artifact bundles the tokenizer rules, normalization dictionary, calibrated threshold, and other metadata in a versioned package recorded in a model registry. The runtime caches vector embeddings for previously seen normalized texts in a key-addressable store and reuses them when the same normalized text appears again. When new site items arrive, the system performs incremental insertion into the approximate nearest neighbor index without a full rebuild. For throughput, vector computations run on a hardware accelerator when available and fall back to a processor implementation while maintaining numerical equivalence within a stored tolerance.

Auxiliary classification and dictionary expansion. For flagged items, a secondary check runs a trained auxiliary classifier that predicts a likely code family and a likely billing category and provides a suggested resolution with a confidence score that is written into the audit record. When an operator confirms or corrects a flagged mapping, the system automatically expands the synonym dictionary with the normalized phrases and re-trains or fine-tunes the embedding function to capture the new equivalence.

Forecasting for future budgets. The system also generates a forecast dataset by aggregating composite score components, selected cost values, code family identifiers, and trial context features from reconciled runs. A predictive regression model trained on this dataset outputs expected site costs for a proposed trial schedule and confidence intervals to inform sponsor-site negotiations.

Why these steps matter in practice. The combination of unit-length embeddings, cosine-based nearest-neighbor retrieval on a navigable small-world index, a code-dominant composite score with calibrated acceptance, and maximum-weight matching on a bipartite graph produces deterministic, auditable reconciliations at scale. Snapshotting with hashes and deterministic run identifiers ensures repeatability. Policy rules provide consistent cost selection under Medicare Coverage Analysis allowances and contract caps, while the auxiliary classifier and operator feedback reduce open items over time.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
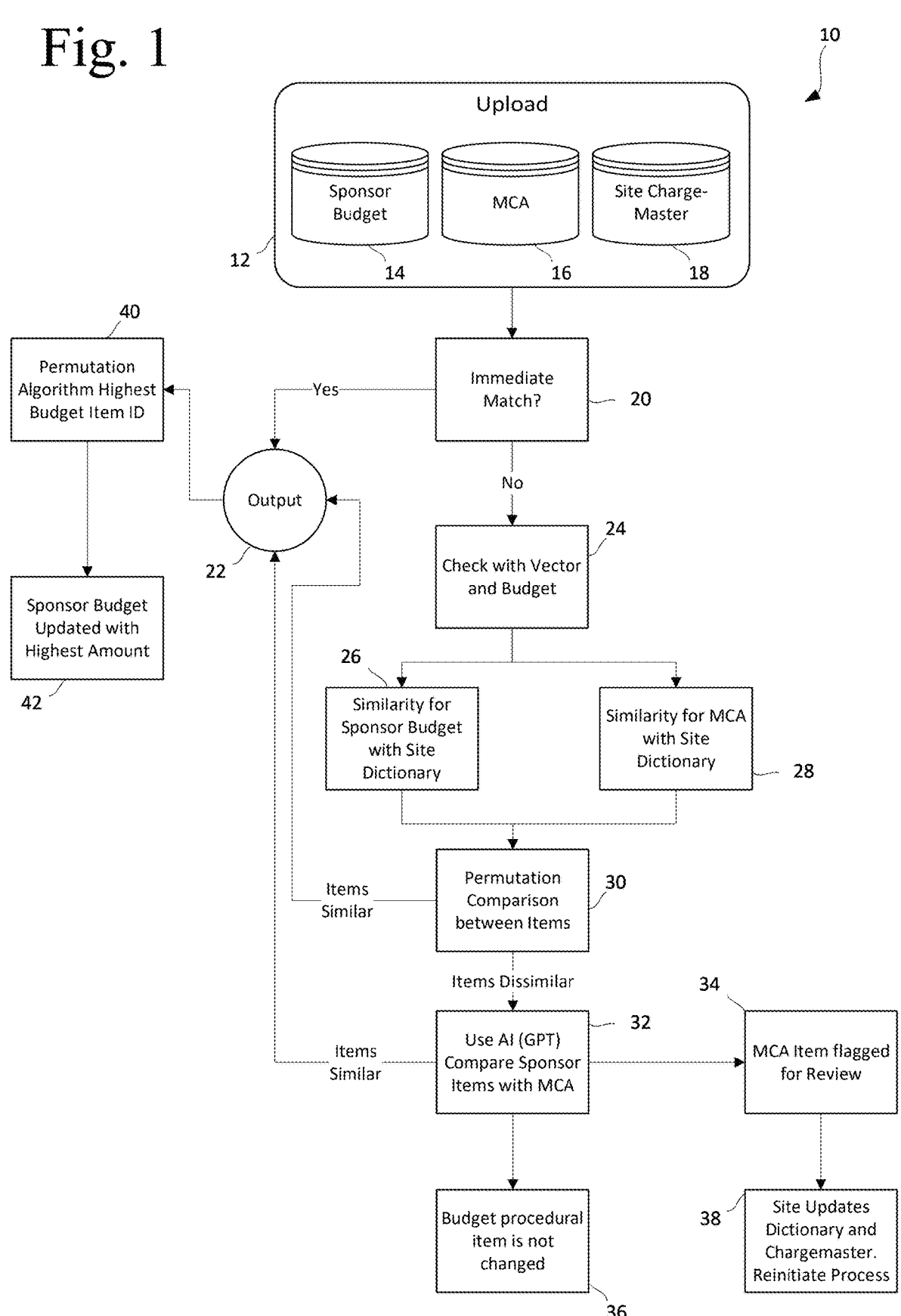
FIG. 1 is a diagrammatic view of a budgeting process according to an embodiment of the invention, showing data ingestion, vector-based analysis, and AI-driven reconciliation to produce a unified clinical trial budget.

The system begins by ingesting procedural and budgetary data from multiple sources, such as a sponsor's budget, Medicare Coverage Analysis (MCA), and clinical site charge masters. Each source provides structured data that includes field identifiers like procedure names, CPT codes, costs, and billing categories. The system ingests this data using a secure API that handles the encrypted transmission of sensitive clinical and financial data. The clinical trial budget templates (e.g., those in Excel format) often follow a tabular structure where each row represents a specific procedure or service, and columns define attributes like procedure name, CPT code, cost, frequency, and billable category. For example, in the sponsor's budget, a row may appear as follows:

TABLE 1

| Procedure Name | CPT Code | Cost | Frequency | Billable Category |
|---|---|---|---|---|
| X-ray, Chest 2 Views | 71020 | $150 | 1 | Research Billable |

This data format is replicated across multiple sources, but terminology and codes may vary between datasets. The system ingests all relevant files (e.g., CSV, Excel, JSON, XML formats) into a central database where they are prepared for vector-based processing.

System Architecture, Secure Ingestion, and Snapshotting

In one embodiment the reconciliation engine executes on a distributed computing platform that includes one or more server machines, each with a multi-core processor, volatile memory, and persistent storage. The platform exposes a secure network interface for ingress and egress of budget data and results. An ingestion controller receives files and API payloads from the sponsor budget source, the Medicare Coverage Analysis source, and the site charge master source. Upon receipt, the controller constructs an immutable ingestion snapshot consisting of: the raw payloads from each source, a source descriptor that includes the origin, transport protocol, and authentication identity, and a monotonic ingestion timestamp. The controller computes a cryptographic hash value over the concatenation of the raw payloads and metadata. The snapshot identifier and hash are stored in append-only storage so that all downstream computations can reference a reproducible view of input data.

The ingestion pipeline normalizes transport differences so that records from CSV, Excel, JSON, and XML are converted into a common internal representation. Each procedural item is assigned a stable internal identifier and is placed into a staging table with typed columns for procedure name, standardized procedure code, cost value, frequency, billing category, and source. Rows that fail schema validation are quarantined with machine-readable reasons and do not enter the reconciliation path until corrected. The staging table is indexed by standardized procedure code and by a normalized textual key as described below.

The system uses secure transport for all remote calls and file transfers. Connections are authenticated with signed tokens or mutual Transport Layer Security. At rest, the snapshot payloads and staging tables are encrypted with keys managed by the platform's key service. Access control lists govern which components can read or write each dataset. Audit events are emitted for every access to protected data. These measures reduce the operational risk of manual handling and ensure compliance with data governance requirements while enabling direct, automated feeds from the participating systems.

To improve throughput, the ingestion controller performs parsing and schema validation in parallel. A task scheduler partitions large files into record chunks and assigns them to worker threads. Each worker writes validated rows to the staging table using batched transactions. When all sources in a snapshot are fully parsed, the controller seals the snapshot and notifies the vectorization service to begin processing. This snapshot-first design ensures that every reconciliation run is deterministic and replayable against a consistent input view.

Vector-Based Semantic Analysis

After ingesting data from all sources, the system converts each procedural item into a vector representation. This conversion process uses a machine learning model—commonly a word embedding model such as Word2Vec or GloVe—pre-trained on large corpora of medical texts. These models map each word or phrase in the procedural description to a high-dimensional vector space. In this space, semantically similar terms (e.g., "X-ray, Chest 2 Views" and "Chest Radiograph") are located close to each other, while unrelated terms (e.g., "MRI of Brain") are placed further apart. For instance, the phrase "X-ray, Chest 2 Views" might be represented as a vector:

$$V_{X\text{-}ray,Chest2Views}=[0.32,0.14,0.56,0.23,\ldots,0.11] \qquad (1)$$

Similarly, "Chest Radiograph" is mapped to a vector:

$$V_{ChestRadiograph}=[0.30,0.15,0.58,0.25,\ldots,0.12] \qquad (2)$$

The similarity between these vectors is calculated using cosine similarity, which measures the cosine of the angle between two vectors. Cosine similarity returns a value between −1 and 1, where 1 indicates identical vectors, 0 indicates orthogonal vectors (no similarity), and −1 indicates completely opposite vectors. For these two terms, the cosine similarity score might be:

$$\text{Cosine Similarity}(V_{x\text{-}ray,Chest2Views}, V_{ChestRadiograph})$$
$$=0.98 \qquad (3)$$

This high similarity score indicates that these two procedural descriptions are nearly identical in meaning, despite slight differences in wording. The system stores these similarity scores in an internal matrix that it will use later for procedural alignment across datasets.

Vector Embeddings and Candidate Retrieval

Following text normalization, the system maps each procedure name to a fixed-length embedding vector that captures semantic content. In one implementation the text-embedding function is a dual-encoder model trained to produce a 256- or 384-dimensional real-valued vector for each input sequence. The numerical attributes of the item, such as cost value and frequency, are incorporated by concatenating scaled numeric features to the text embedding or by projecting them through a small feed-forward network and summing the projection with the text vector. Each resulting vector is L2-normalized to unit length and stored in a contiguous array of 32-bit floating point values. This layout improves cache locality during similarity computations.

To avoid quadratic comparisons the system builds an approximate nearest neighbor index over the site vectors. In one embodiment the index is a navigable small-world graph with parameters that bound both memory and runtime. The index is constructed with a maximum node degree M and a construction effort parameter that controls neighbor consolidation. Query-time search effort is governed by a parameter that limits the number of node expansions per search. These parameters bound fan-out so that per-query latency grows sublinearly with the number of indexed items. The index supports incremental insertion so that newly added site procedures can be introduced without rebuilding the whole structure. The index also provides a delete-and-relink operation for retired items.

For each sponsor item the engine performs a top-k neighbor query against the index to retrieve a ranked candidate list of site items by cosine similarity. Cosine similarity between two unit vectors u and v is computed as the dot product u.v, which equals 1 for identical vectors and approaches 0 as vectors diverge. The retrieved list is passed to a scoring stage that considers code and billing signals in addition to textual similarity. The Medicare Coverage Analysis dataset is queried similarly when aligning a matched sponsor-site pair to a Medicare Coverage Analysis item.

The engine optionally precomputes and caches vector embeddings for frequent procedure names and abbreviations in a key-addressable store. When an identical normalized text appears in a later reconciliation run the cached vector is reused. The cache is versioned with the embedding model identifier so that updates to the model invalidate old cache entries automatically.

Permutation-Based Re-Tokenization

When a sponsor item fails to find a candidate that satisfies a minimum similarity bound, the engine generates alternative tokenizations by expanding or rewriting abbreviations and by permuting multi-segment phrases. For example, "abdomen and pelvis CT with contrast" yields variants that place "with contrast" at the end or expand "CT" to "computed tomography." Each variant is re-embedded and re-queried. The process halts when a candidate meets the threshold or when the variant budget is exhausted, after which the item is flagged for manual review with the top candidate explanations.

Matching Based on CPT Codes

While semantic similarity between procedural descriptions is valuable, the system also evaluates exact matches based on CPT codes, which are standard identifiers for medical procedures. For example, in one dataset, the system might find a match for CPT code 71020 ("X-ray, Chest 2 Views") in both the sponsor's budget and the site charge master. However, in the MCA, the corresponding procedure might be listed under a different CPT code, such as 71010 ("Radiograph of Chest").

To reconcile such discrepancies, the system applies a hierarchical weighting approach. Exact matches on CPT codes receive higher priority over semantic matches. For instance, an exact CPT code match would be weighted more heavily than a semantic match, even if the procedural descriptions differ slightly. If the system finds that CPT code 71020 exists in both the sponsor's budget and the site's charge master, it will prioritize this match, while the differing code in the MCA (71010) would be flagged for further review.

Composite Match Score and Calibration

The system computes a composite match score S for each candidate pair that aggregates code equality, textual similarity, numeric proximity, and billing consistency. In one embodiment:

$$S = w_{code} \cdot I_{code} + w_{txt} \cdot sim_{cos} + w_{num} \cdot e^{-\frac{|c_s - c_t|}{\sigma}} + w_{bill} \cdot I_{bill}$$

Where $I_{code}$ equals 1 when standardized procedure codes match exactly and equals 0 otherwise, $sim_{cos}$ is the cosine similarity between the embedded vectors, $c_s$ and $c_t$ are the cost values of the sponsor and site items, $\sigma$ is a scale parameter that controls sensitivity to price gaps, and $I_{bill}$ equals 1 when the billing categories are compatible under stored policy rules. The weight vector $W=\{w_{code}, w_{txt}, w_{num}, w_{bill}\}$ is constrained such that $w_{code}$ exceeds every other component weight, which causes exact code equality to dominate the score when present.

The engine accepts a candidate pair when S meets or exceeds a calibrated threshold t. The threshold is selected by offline analysis on a held-out validation set of historical reconciliations. The calibration procedure sweeps t and records precision, recall, and false positive rates. An operator selects t to satisfy target accuracy criteria and stores t together with the weight vector and the embedding model identifier in model metadata. During runtime the scoring stage uses the stored metadata to ensure consistent decisions across reconciliation runs.

Code-Family Gating

To prevent spurious influences from unrelated codes, the score boost from a Medicare Coverage Analysis alignment is applied only when the Medicare Coverage Analysis item shares a code family with either the sponsor item or the site item. A code family is a stored grouping of standardized procedure codes that have known hierarchical relationships or clinical equivalence. If the Medicare Coverage Analysis code does not share a family with the sponsor or site code, the code-related component for that alignment is set to zero.

Machine Learning for Contextual Understanding

In cases where neither a semantic nor a CPT code match exists, the system resorts to a machine learning model, typically a transformer-based architecture such as BERT (Bidirectional Encoder Representations from Transformers) or a fine-tuned GPT (Generative Pretrained Transformer). These models excel at contextual understanding and can identify deeper relationships between procedural items that might not be captured through simple vector-based analysis.
Secondary Check and Auxiliary Classifier.

For each flagged item the engine applies a trained auxiliary classifier that predicts (i) a likely code family and (ii) a likely billing category based on the normalized text, the top-k candidate embeddings, and metadata from the sponsor and site sources. The classifier outputs calibrated confidence scores using temperature scaling on a validation set. The system writes the predicted code family, the predicted billing category, and the associated confidence scores into the audit record and presents them in the operator console as a suggested resolution.

For instance, suppose a sponsor's budget lists "MRI of the Brain" and the MCA lists "Magnetic Resonance Imaging of the Head." The semantic similarity between these terms might be lower than expected due to the difference in terminology. However, the transformer model is capable of learning that both descriptions refer to the same procedure by analyzing the context in which the terms are used. The model performs this analysis by breaking down the procedural descriptions into tokens (words or sub-words) and attending to the relationships between these tokens. Through multiple iterations (or epochs), the model refines its understanding of these relationships, enabling it to detect that "MRI of Brain" and "Magnetic Resonance Imaging of Head" are functionally equivalent.

For practical implementation, the model would typically be trained on tens of thousands of procedural descriptions from various clinical trial datasets. Each epoch of training represents one complete pass through the training data. For example, after 50 epochs of training, the model might achieve an accuracy rate of 98%, meaning that it can correctly identify procedural matches 98% of the time. The number of epochs and the size of the training data are tuned to balance computational efficiency with model accuracy.

In some deployments, the secondary check further invokes a large-language-model to generate natural-language rationales for the top candidate(s), including salient token overlaps, code-family context, and price-range consistency. These rationales are written with the candidate scores to the audit record and surfaced to an operator to accelerate review; the model's output does not override acceptance thresholds or graph matching and is advisory only.
Handling Numerical Attributes and Costs The system is also designed to handle numerical attributes such as procedural costs, which vary between datasets. These cost variations are reconciled by evaluating not only the procedural descriptions but also the associated pricing structures. For example, the sponsor's budget may list "X-ray, Chest 2 Views" with a cost of $150, while the site's charge master lists the same procedure at $180. The system calculates the average cost for similar items, adjusts for discrepancies based on procedural codes, and updates the reconciled budget accordingly.
Policy Rule Engine for Cost and Billing Resolution A policy rule engine determines the selected cost value and resolved billing category for each matched set. Rules are expressed as condition-action statements that operate on fields from the matched sponsor, site, and Medicare Coverage Analysis items. For research billable items the engine selects the site cost value unless a contract cap applies. Caps are specified as absolute maxima or as percentages over reference rates. When a cap is enforced, the engine stores a cap-enforcement flag and the reference that triggered it. For standard of care items the engine selects the Medicare Coverage Analysis allowed amount when present. If the Medicare Coverage Analysis provides a range, the engine selects the allowed amount appropriate to the trial setting based on stored coverage guidelines. If the sponsor designates an item as non-billable the engine selects a zero cost value and records the designation in provenance fields.

Conflict resolution is implemented via a priorities table that can be parameterized by code family and context (e.g., imaging vs. site-specific services, inpatient vs. outpatient). The rule engine evaluates conditions deterministically under the run's snapshot token and records, in the audit report, the priority row applied, the input facts considered, and the resulting selected cost and billing category.

The engine also resolves billing category disagreements. If the sponsor marks an item research billable while the Medicare Coverage Analysis marks it standard of care, the engine consults a priorities table that can prefer Medicare Coverage Analysis determinations for certain code families while preserving sponsor designations for others. The rule that resolved a conflict is recorded with a rule identifier and the input facts used.

In some cases, cost variations might be significant due to differences in billing categories, such as "research billable" versus "standard of care." The system uses machine learning to classify each procedure into its appropriate billing category based on historical data. For example, if a procedure has frequently been categorized as "standard of care" in past trials, the system will automatically assign it to this category unless evidence suggests otherwise. By integrating these billing classifications, the system ensures that the reconciled budget reflects not only the most accurate procedural matches but also the appropriate financial allocations.
Iterative Learning and Model Updates One of the key strengths of this system is its ability to continuously learn and improve. Each time the system processes a new clinical trial budget, it incorporates feedback from the reconciliation process into its machine learning model. For instance, if the system initially fails to match "Ultrasound of the Heart" with "Echocardiogram," but a user manually corrects this mismatch, the system records this correction and updates its internal dictionary of procedural terms. Over time, the system builds a more comprehensive understanding of procedural terminology, improving its accuracy in future reconciliations.
Active Learning Loop and Dictionary Expansion The engine incorporates an active learning loop that uses user feedback on flagged items to improve future reconciliations. When an operator confirms a match or corrects a suggested mapping, the system writes a feedback event that includes the normalized texts, codes, billing categories, and the operator's decision. A trainer service periodically aggregates feedback events and uses them in three ways. First, it schedules additional fine-tuning of the embedding model on the new positive and negative pairs, with class weights that emphasize recent errors. Second, it expands the synonym dictionary by recording pairs of normalized phrases that were confirmed to be equivalent. Third, it re-estimates calibration parameters by recomputing the acceptance threshold to maintain target precision and recall in light of the updated embeddings and synonyms.

Model promotion is gated by quality guardrails. A candidate model must meet or exceed prior performance on a fixed benchmark set and must not degrade performance beyond allowed tolerances for specific code families that are known to be sensitive. On promotion, the model registry assigns a new active version and signals the reconciliation services to refresh caches and indexes that depend on the embeddings. This controlled loop reduces manual workload over time while ensuring stable behavior.

This iterative learning process is facilitated by a feedback loop, where users provide input on unresolved items flagged by the system. For example, if a procedure in the sponsor's budget cannot be matched with any corresponding item in the MCA or site charge master, the system flags this item for manual review. Once a user resolves the issue (e.g., by adding a new procedural term or CPT code to the dictionary), the system updates its machine learning model accordingly. In the next iteration, the system will automatically recognize similar discrepancies and resolve them without manual intervention.

Quantitative Examples and Real-World Application

To illustrate the system's functionality, consider a more detailed example involving a clinical trial with multiple procedures across different sites. In the sponsor's budget, the procedure "CT scan of chest" is listed with a cost of $500 and CPT code 71250. In the MCA, the corresponding procedure is listed as "Chest CT," with a cost of $480 and CPT code 71260. In the site's charge master, the procedure appears as "Thoracic CT scan" with a cost of $520 and CPT code 71250.

The system processes each of these descriptions using vector-based semantic analysis and machine learning. The cosine similarity between "CT scan of chest" and "Chest CT" is calculated to be 0.89, reflecting a moderate level of similarity. However, the CPT code mismatch between 71250 and 71260 reduces the overall similarity score for the MCA entry. By contrast, the site's charge master entry has both a high cosine similarity score (0.95) and an exact CPT code match, leading the system to prioritize this entry in the reconciled budget.

After reconciling the data, the system generates the following unified output:

TABLE 2

| Procedure Name | CPT Code | Cost | Source | Similarity Score |
|---|---|---|---|---|
| CT scan of chest | 71250 | $520 | Site Charge Master | 0.95 |
| Chest CT | 71260 | $480 | Medicare Coverage | 0.89 |
| CT scan of chest | 71250 | $500 | Sponsor Budget | 0.95 |

The system selects the maximum permitted value under policy rules of $520 from the site charge master, given its high similarity score and the exact CPT code match. The Medicare Coverage Analysis (MCA) entry with the slightly lower similarity score (due to the CPT mismatch) is flagged for further review but not automatically included in the reconciled budget. This flagging allows users to manually inspect cases where similar procedures might differ due to regulatory or regional cost discrepancies.

One-to-One Assignment Via Weighted Bipartite Matching

When multiple site candidates could match a single sponsor item, the engine enforces a one-to-one mapping by constructing a weighted bipartite graph. Left nodes represent sponsor items, right nodes represent site items, and edges connect only those pairs whose composite match score meets or exceeds the calibrated threshold. Edge weights equal the composite match score for the pair. The engine computes a maximum-weight matching across this graph to select a set of non-overlapping pairs that maximizes overall confidence. In one implementation the matching is computed by the Hungarian algorithm operating on a dense score matrix, with infinite cost assigned to disallowed pairs so they cannot be selected. Ties are broken deterministically using a stable key that includes the ingestion timestamp, source identifiers, and lexical order of normalized names. This assignment prevents duplicate site items from being counted multiple times and ensures a consistent, reproducible reconciliation outcome.

In real-world applications, this kind of precision in handling procedural data is invaluable for large multi-site trials, where discrepancies between institutional pricing and procedural descriptions can create confusion and delays in budget negotiations. The system not only automates the detection of mismatches but also provides users with a transparent view of how those mismatches were addressed, making it easy to trace decisions back to specific vector similarities and CPT code analyses.

Integration with Machine Learning Models

In addition to vector-based semantic analysis, the system incorporates more advanced machine learning algorithms to enhance its matching and classification capabilities. As mentioned earlier, transformer-based architectures like BERT (Bidirectional Encoder Representations from Transformers) are especially effective for understanding the context in which procedural terms are used. This capability is key when the system encounters nuanced variations between terms that are not captured solely by their surface-level wording.

For example, let's take two procedural descriptions: "CT scan of thorax with contrast" and "Computed tomography of chest using contrast." Both refer to the same medical procedure, yet their wording and structure differ. A transformer-based model processes the entire description by encoding each token (word or sub-word) and understanding the relationship between these tokens. The transformer model learns to focus on the context provided by surrounding words (e.g., the fact that "contrast" in both descriptions indicates that the procedures involve similar imaging techniques). Through multiple training epochs, the model becomes adept at recognizing such procedural similarities, even when the descriptive wording differs significantly.

For practical implementation, a large dataset of procedural descriptions can be used to pre-train the model. Each description is tagged with its corresponding CPT code and cost, enabling the model to learn both the linguistic and numerical aspects of each procedure. Once trained, the model achieves high accuracy in distinguishing between similar and dissimilar procedures, even in cases where the semantic differences are subtle. By way of example, after training, the model may correctly match "Ultrasound-guided biopsy of liver" with "Sonography-assisted liver biopsy," despite these phrases having different lexical structures.

The machine learning model further improves over time through continuous feedback loops. Every time the system encounters a new procedural term or mismatch that it cannot automatically reconcile, it flags the entry for manual review. Once a human reviewer intervenes and provides the correct match, the system updates its internal dictionary and retrains the model based on this new data. This iterative process ensures that the system continually evolves, reducing the need for manual intervention over time.

Performance Engineering, Caching, and Incremental Index Maintenance

The reconciliation engine is engineered for real-time or near real-time performance. Vector computations execute on a hardware accelerator when available and fall back to a processor implementation otherwise. Both paths are numerically aligned within a stored tolerance. A vector cache stores embeddings for frequent normalized phrases and abbreviation expansions. Cache entries include the model version and the normalized text so that a model upgrade invalidates only incompatible entries.

The approximate nearest neighbor index supports incremental maintenance. When a site catalog changes the system computes embeddings for new items and inserts them into the graph index without rebuilding unaffected regions. A background task periodically rebalances the graph to maintain desired average degree and search cost. Rebalancing is performed against a maintenance snapshot and then atomically swapped into service to avoid query disruptions.

For concurrency control, each reconciliation request acquires a snapshot token that fixes the versions of the model, synonym dictionary, calibration weights, and index used for the run. All processing for the request uses the same token, which guarantees that top-k candidates, scores, and matches remain consistent throughout the run even if background updates occur.

Training and Iteration

The system's machine learning components are trained using a supervised learning approach, where labeled data consisting of procedural terms, CPT codes, and costs are fed into the model. Each data point is annotated with its correct matches, allowing the model to learn the relationships between terms and codes over many iterations. A typical training process might involve thousands of procedural terms, each with slight variations in wording. For instance, one training batch might include terms like "X-ray, Chest 2 Views," "Chest Radiograph," and "Radiograph of Chest 2 Views." The model learns through trial and error, refining its internal weights based on feedback from the training data.

During training, the system runs through several epochs, where each epoch represents one complete pass through the training dataset. For a large dataset, the system may run between 50 and 100 epochs, gradually improving its accuracy with each iteration. After each epoch, the system evaluates its performance using a validation set, which consists of new procedural descriptions that the model has not seen before. This evaluation allows the system to measure its accuracy in matching terms, aligning CPT codes, and selecting appropriate costs for each procedure. Over time, the model achieves an accuracy rate that can exceed 95%, meaning that it correctly matches and reconciles procedural items in the vast majority of cases.

The model's architecture plays a critical role in its ability to handle complex, real-world clinical trial data. Transformer models are particularly well-suited for this task because they can handle long-range dependencies between words. For example, in a phrase like "MRI of brain without contrast," the model needs to understand that "without contrast" modifies "MRI" and should be taken into account when determining the procedure's cost and billing category. Transformer models excel at this kind of contextual understanding, making them ideal for clinical trial budget reconciliation, where subtle differences in procedural descriptions can have significant financial implications.

Labeling Workflow and Quality Control

For supervised training and evaluation the system provides a labeling interface that displays anchor and candidate items together with their composite score components. Two independent reviewers label each pair as match or nonmatch. A conflict resolver adjudicates disagreements or routes them to a third reviewer. The system computes inter-annotator agreement and uses it to weight examples during training so that highly consistent labels exert greater influence on the learned embeddings. Review screens omit any fields that are unnecessary for the semantic task and redact free-text notes to avoid exposing unrelated information. The tool records reviewer identity, decision time, and reasons selected from a controlled vocabulary. These logs support audits of training data provenance and demonstrate that the learned models were derived from curated and de-identified examples.

Real-World Integration

Once the system has processed all available procedural data and performed its vector-based and machine learning-driven analyses, it generates a reconciled budget in a structured format. This output format can be tailored to the needs of the clinical trial management team, with common formats including JSON, XML, or Excel files. These formats are designed to integrate seamlessly with existing clinical trial management systems (CTMS), allowing for real-time updates to budgets as new data becomes available.

API Schemas, Idempotency, and Security

The system exposes an API to submit source datasets and retrieve reconciled outputs. A submission request includes a header with authentication credentials and an idempotency key. If an identical idempotency key is received again within a retention window, the system returns the original response rather than reprocessing the request. The payload includes structured arrays for sponsor items, Medicare Coverage Analysis items, and site items. Each item contains fields for procedure name, standardized procedure code, cost value, billing category, and optional frequency. The service responds with a reconciliation identifier and a processing status. Callers may poll a status endpoint or register a webhook to receive completion notifications.

On completion the system provides a machine-readable payload, for example a JSON document, that includes for each reconciled set: the resolved procedure name, resolved standardized procedure code, resolved billing category, selected cost value, and provenance fields that identify which source contributed the selected cost. For each flagged item the payload includes the top candidate explanations and composite score breakdown. A separate audit endpoint serves detailed audit records for authorized clients.

All API connections require Transport Layer Security. Clients authenticate with signed tokens and may optionally use mutual Transport Layer Security with client certificates. Role-based authorization controls whether a client can submit, view results, or retrieve audit records. Rate limiting protects service availability. The service records the caller identity, timestamp, and ingestion snapshot identifier for every API call to maintain a complete operational trace.

For example, in a large multi-site clinical trial, budget data from each participating site is continuously updated as the trial progresses. The system ingests new data and automatically adjusts the reconciled budget based on any procedural changes or cost fluctuations. If a site adds a new procedure that was not previously included in the budget (e.g., an advanced imaging technique), the system processes this new entry, calculates its vector similarity to existing procedures, and determines the appropriate cost based on historical data. If the new procedure cannot be matched to any existing entries, the system flags it for manual review and updates its dictionary once the correct match is identified.

The system's flexibility allows it to adapt to a wide range of clinical trial settings. Whether the trial involves a single site or dozens of locations across different regions, the system ensures that all procedural items are reconciled accurately, reducing the risk of billing errors or cost discrepancies. This real-time reconciliation process is particularly valuable in trials where budgets are tightly controlled and must be regularly updated to reflect the actual costs incurred by participating sites.

In more complex trials, where the same procedure might be described differently across multiple sites, the system's machine learning model plays a critical role in identifying and resolving these discrepancies. For instance, if one site refers to a procedure as "CT scan of abdomen and pelvis," while another site lists it as "Abdominal and pelvic CT," the model recognizes the equivalence between these terms, calculates their vector similarity, and assigns the correct CPT code and cost based on historical data. This level of precision ensures that the reconciled budget accurately reflects the procedures being performed at each site, while also maintaining consistency across the entire trial.

Continuous Feedback and Improvement

The system's ability to learn from its own performance is a key feature that sets it apart from traditional budget reconciliation methods. Each time the system encounters a mismatch or procedural term that it cannot automatically reconcile, it flags the item for manual review. Human reviewers can then provide feedback, correcting the system's output and updating the internal dictionary and machine learning model accordingly. This feedback loop ensures that the system continually improves, reducing the need for manual intervention over time.

For example, if a human reviewer identifies a new procedural term that the system has not seen before (e.g., "Ultrasound-guided liver biopsy"), the reviewer can manually match this term with an existing entry in the system's dictionary or add it as a new entry. The system then updates its internal model to recognize this term in future budget reconciliations, ensuring that it can automatically process similar entries without requiring further manual input.

This continuous improvement process is particularly valuable in the context of clinical trials, where new medical procedures and technologies are constantly being introduced. By incorporating feedback from human reviewers, the system stays up to date with the latest advancements in medical technology, ensuring that it can accurately process even the most cutting-edge procedures.

Audit Trail and Tamper Resistance

Every reconciliation produces an audit record per processed item. The record contains the ingestion snapshot identifier and hash, the embedding model version, the synonym dictionary version, the calibration weight vector and threshold version, the normalized texts, a compact vector fingerprint for each embedding, the top candidate list and their component scores, the match or flag decision, the selected edge in the bipartite matching with weight, the cost and billing rule decisions, and any secondary classifier recommendation with confidence. The vector fingerprint is a stable quantized representation or hash of the unit vector that enables later verification without exposing the full floating-point values. Each reconciliation run is labeled with a deterministic run identifier computed as a cryptographic hash over the tuple (ingestion snapshot hash, embedding model version, synonym dictionary version, calibration weight vector identifier, threshold identifier, index version). The run identifier appears in every audit record and in the API response so that any result can be replayed and verified against the recorded versions.

Audit records are written to append-only storage and are signed with a service key. A replay utility reconstructs a reconciliation from the audit records, re-runs the scoring and matching with the recorded versions, and verifies that the outputs match within numerical tolerances. The utility reports any divergence and identifies the step that produced it. This capability provides strong guarantees that the system's outputs are explainable, reproducible, and tamper-evident. The append-only store enforces time-stamped, version-controlled entries with user/role attribution and cryptographic signing consistent with practices used to meet 21 CFR Part 11 requirements for electronic records and audit trails. Audit records and associated model/policy artifacts are retained for at least the policy-configured retention period, and a replay utility verifies equivalence within stored numeric tolerances (e.g., absolute or ULP-bounded differences for floating-point operations) while reporting any divergence and the step at which it occurs.

Turning now to FIG. 1, the process as a whole is denoted by reference numeral 10. Initially, the system ingests an upload 12, which contains the procedural data from various sources including the sponsor's budget 14, Medicare Coverage Analysis (MCA) 16, and the site charge master 18. Each of these datasets may contain differing procedural descriptions, CPT codes, and cost information, which must be reconciled to produce an accurate clinical trial budget.

After the data is ingested, the system checks for an immediate match between the procedural items across these datasets. This step is denoted by 20. If a direct match is found, the system generates the final reconciled budget and proceeds to the output step, denoted by 22.

In the case where no immediate match is found, the system invokes additional processing steps. The first of these steps involves performing a check with vector and budget (24). This step involves using a vector-based similarity algorithm to compare the procedural descriptions from the sponsor's budget and the MCA against an internal dictionary of known terms within the system.

Next, the system calculates the similarity for the sponsor's budget with the site dictionary (26) and the similarity for the MCA with the site dictionary (28). These similarity scores are derived using cosine similarity or another vector-based similarity measure. The goal of these steps is to assess how closely the procedural descriptions align between the sponsor's budget, the MCA, and the site charge master.

If the similarity score is insufficient to determine a match, the system proceeds to the permutation comparison between items (30), where different combinations of procedural terms are tested to identify potential matches. This permutation algorithm allows the system to detect matches even when procedural descriptions vary slightly across datasets.

For more complex cases, the system utilizes AI, specifically GPT (Generative Pretrained Transformer), denoted by 32, to further evaluate the context of the procedural descriptions and identify deeper semantic similarities between the items. A transformer model analyzes the linguistic structure and context of the procedural terms, enhancing the system's ability to detect equivalent items that might not be captured by basic vector similarity measures.

If, after these checks, the system still finds that items in the MCA and sponsor budget are dissimilar, the MCA item is flagged for review (34). At this point, manual intervention may be required to resolve the discrepancy between datasets.

If the system determines that the procedural items are similar or identical after analysis, the budget procedural item is not changed (36), and the system continues to the next item. In cases where the system identifies discrepancies, the site updates its dictionary and charge master (38), incorporating the new information to ensure better alignment in future budget reconciliations. After updating the dictionary, the system reinitiates the process from the beginning to verify that the reconciliation is correct.

The final step in FIG. 1 involves the permutation algorithm identifying the highest budget item ID (40). Once the system selects the item with the maximum permitted value under policy rules, it updates the sponsor's budget to reflect this value. This is the sponsor budget updated with the highest amount (42), ensuring that the final reconciled budget compensates the site at the highest rate allowable for each procedure.

Figure 2:
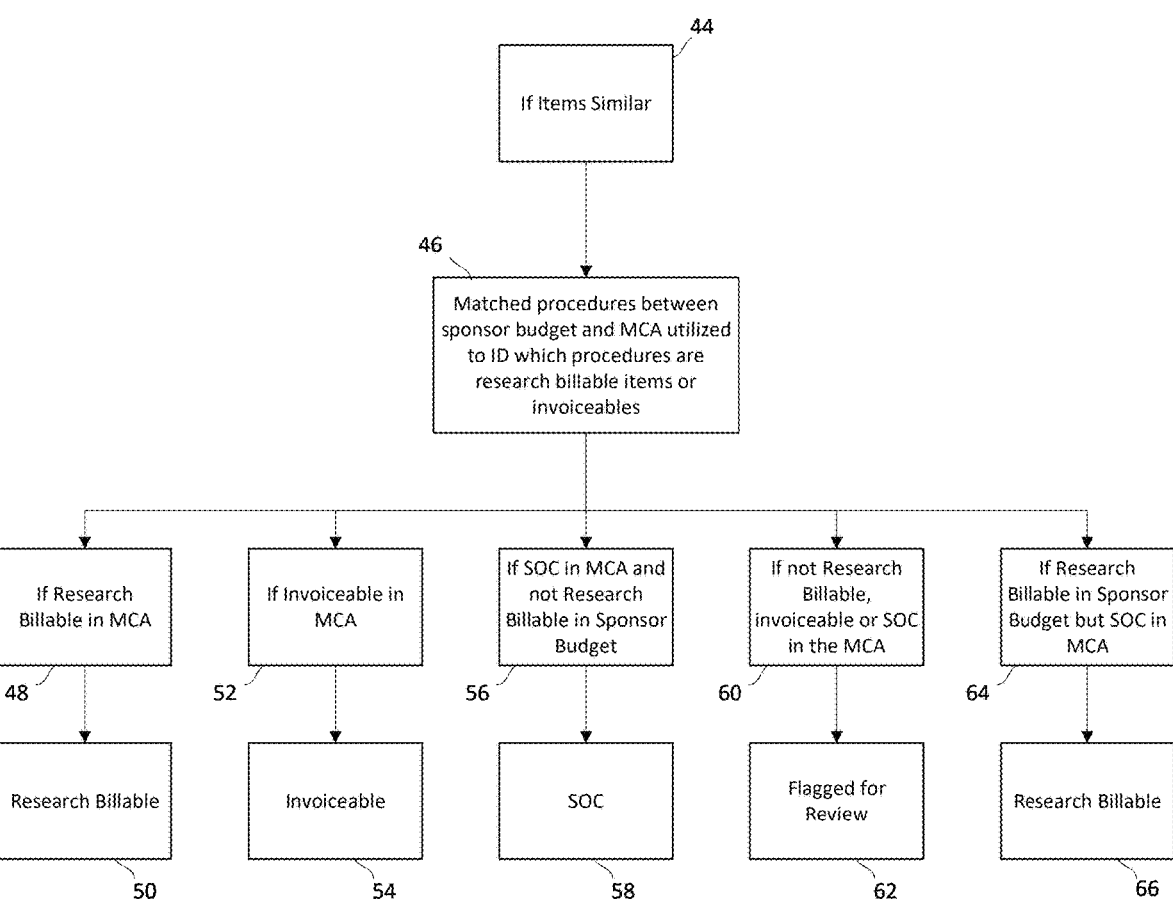
FIG. 2 is a diagrammatic view of a reconciliation process according to an embodiment of the invention in which matched procedural items are categorized into specific billing categories, such as research billable, invoiceable, and standard of care (SOC).

Turning now to FIG. 2, the process continues from the outcome where items are determined to be similar, as denoted by reference numeral 44. This step indicates that the system has successfully matched procedural items between the sponsor's budget and the Medicare Coverage Analysis (MCA) through vector-based analysis and CPT code alignment. Once the items are confirmed as similar, the system begins the process of categorizing each procedural item according to its billing status.

At reference numeral 46, the matched procedural items are analyzed to identify whether they are research billable, invoiceable, or related to standard of care (SOC) charges. The system determines this by comparing the information from both the sponsor's budget and the MCA. The decision-making process is driven by predefined rules and billing guidelines that help categorize each item based on its coverage under Medicare and its designation within the sponsor's budget.

The first determination is made at 48, where the system checks whether the procedural item is classified as research billable in the MCA. If the MCA indicates that the procedure is eligible for research billing, the system assigns it to the research billable category, denoted by 50. This ensures that the cost of the procedure will be covered by the research budget, typically funded by the trial sponsor.

If the procedural item is invoiceable per policy/sponsor terms, as denoted by reference numeral 52, it is categorized as invoiceable at 54. These are procedures that may not fall under research-related costs but are instead eligible for invoicing based on standard billing practices. The system identifies these procedures and ensures that they are billed according to the guidelines specified in the MCA.

For procedures classified as SOC in the MCA but not research billable in the sponsor's budget, indicated by 56, the system assigns these items to the SOC (standard of care) category, shown at 58. Standard of care procedures are those that would be provided to patients regardless of their participation in the clinical trial. These costs are generally covered by Medicare or the patient's insurance, rather than being charged to the sponsor.

In some cases, the system identifies items that are not research billable, invoiceable, or SOC in the MCA, denoted by 60. Such items are flagged for further manual review, as indicated at 62. This flagging process allows users to examine these procedural items more closely, often because there is ambiguity regarding how they should be billed or because the item's classification may differ between the MCA and the sponsor's budget.

A unique scenario occurs when a procedure is classified as research billable in the sponsor's budget but SOC in the MCA, denoted by 64. In this situation, the system categorizes the item as research billable at 66, but it may also be flagged for review to ensure that all billing guidelines are followed appropriately. This category ensures that any discrepancies between the sponsor's budget and MCA classifications are captured and reconciled appropriately during budget negotiations.

Figure 3:
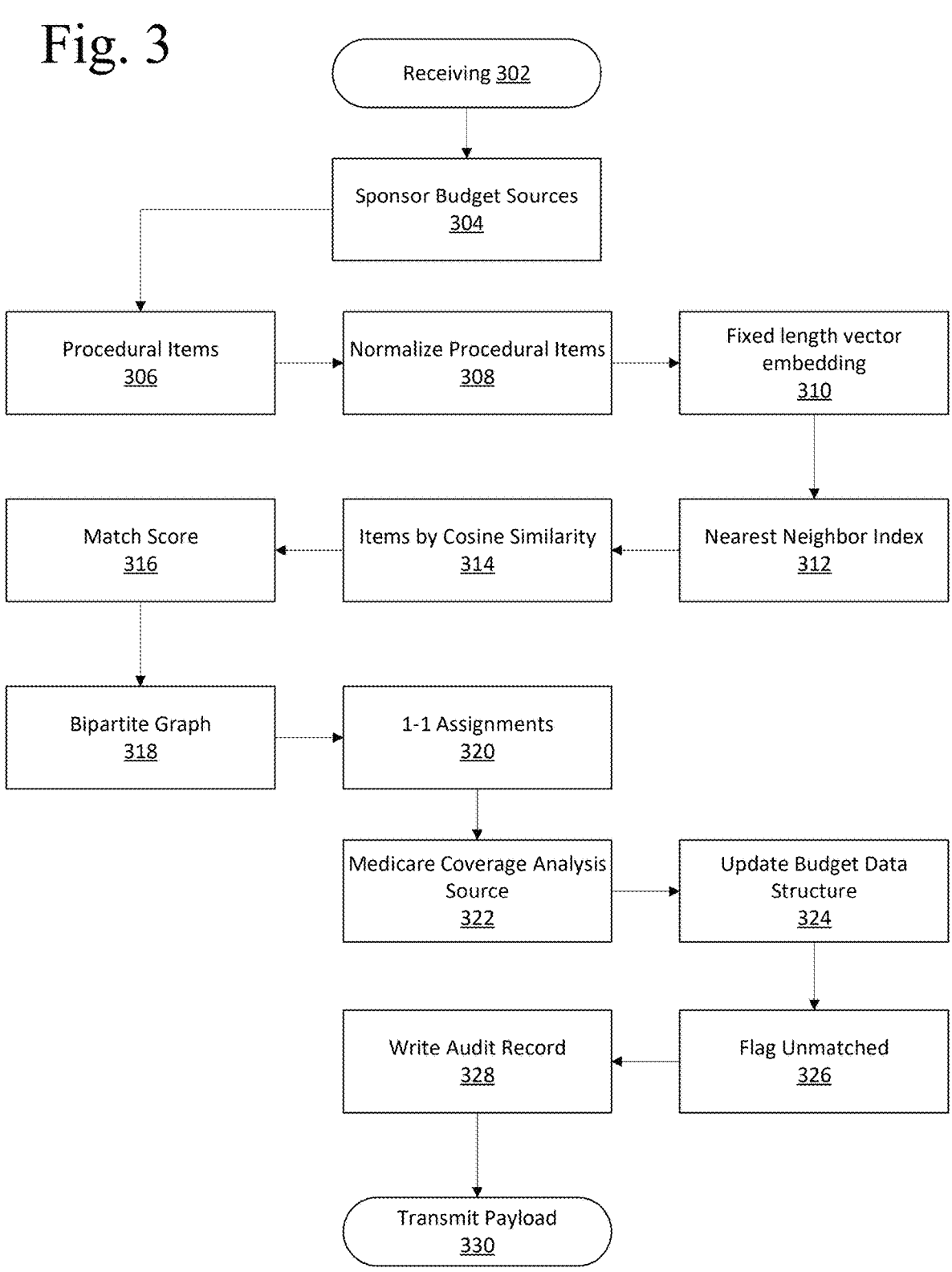
FIG. 3 is a diagrammatic view of a reconciliation pipeline according to an embodiment of the invention, illustrating receipt of source datasets, normalization and embedding of procedural text, candidate retrieval and scoring, maximum-weight matching, Medicare Coverage Analysis (MCA) alignment, policy-based budget resolution, item flagging and audit logging, and transmission of a machine-readable payload.

Turning now to FIG. 3, the process begins at receiving 302, where the system accepts a submission through an authenticated interface. The submission identifies coordinated sources and provides arrays of structured records. In one embodiment the request includes an idempotency key so that identical submissions within a retention window result in the prior response without reprocessing. A reconciliation snapshot is established at this point so that all downstream operations observe a consistent view of the sources.

Sponsor budget sources 304 symbolize one of the feeds delivered at receiving 302. In typical deployments, site charge master records and MCA entries arrive in the same submission; the figure isolates the sponsor feed to emphasize the per-item loop driven by sponsor entries. Each received record preserves at least a procedure name, a standardized procedure code, a cost value, and a billing category for later stages.

Procedural items 306 denote the plurality of received records instantiated in memory under a common schema. Each record is assigned a stable internal identifier. Records that fail schema or type validation can be quarantined and excluded from reconciliation until corrected. Valid items are staged for normalization, embedding, and matching.

Normalize procedural items 308 prepares text and codes for model consumption. Procedure names are tokenized, lowercased, stripped of punctuation, and expanded using a stored synonym dictionary. Codes are mapped to canonical code families so that near-equivalent variants are treated consistently across sources. The normalized text and canonical codes are written to the staging store and may be cached with the dictionary version for audit and replay.

Fixed-length vector embedding 310 converts each normalized description—optionally augmented with scaled numeric attributes such as cost or frequency—into a unit-norm vector using a trained text-embedding function. Hardware acceleration may be used where available with a CPU fallback path that yields numerically equivalent results within a stored tolerance. Embeddings for frequently seen normalized phrases may be cached with model-version keys to reduce latency on subsequent runs.

Nearest neighbor index 312 represents an approximate nearest neighbor structure maintained over vectors for site charge master items. In one embodiment the index is a navigable small-world graph configured with a bounded maximum node degree and a query effort parameter that limits node expansions and yields sublinear retrieval. New site entries can be inserted incrementally without rebuilding the entire index, and background maintenance can rebalance links to preserve recall and latency targets.

Items by cosine similarity 314 retrieves candidates for each sponsor item by querying the index 312. Because embeddings are L2-normalized to unit length, similarity reduces to a dot product that equals cosine similarity. A fixed top-k list can be returned for each query, and downstream scoring is computed only for these candidates to bound runtime. Accelerator kernels may be used for the dot-product calculations.

Match score 316 evaluates each sponsor-site candidate pair with a composite score. The score integrates (i) a code-equality indicator, (ii) the cosine similarity of the vectors, (iii) a numeric proximity term that decays with absolute cost differences according to a tunable scale, and (iv) a billing-consistency indicator derived from the respective categories. Component weights are drawn from stored calibration, with the code-equality weight configured to dominate when exact standardized codes are equal. A candidate is accepted to the next stage when its score meets or exceeds a calibrated acceptance threshold derived from historical validations. In some embodiments, influence from MCA alignment is gated by code-family membership so that unrelated codes cannot boost a score.

Bipartite graph 318 is then formed with sponsor items on the left and site items on the right. Edges exist only for pairs whose composite score met the acceptance threshold, and each edge weight equals that score. The graph, eligible edges, and weights are retained for auditability.

1-1 assignments 320 selects non-overlapping matches by computing a maximum-weight matching over the graph of 318. In one embodiment a Hungarian-style algorithm operates on a finite cost matrix derived from candidate scores, with deterministic tie-breaking so that repeated runs under the same versions yield identical outcomes. Sponsor items not covered by the matching proceed to additional text handling before final disposition.

Medicare Coverage Analysis source 322 aligns each accepted sponsor-site pair to an MCA entry. Alignment can occur by exact standardized code equality or by reapplying the same embedding-and-retrieval pipeline using an MCA vector set. When an MCA code equals the sponsor or site code and shares a code family with that code, the system can adjust confidence for the pair. MCA entries that do not share a family with either code are gated from influencing the match.

Update budget data structure 324 resolves financial terms for each matched set. A rule engine selects a cost and determines the resolved billing category under a machine-readable policy. Illustrative policies include selecting the site's cost for research-billable items, subject to any negotiated caps, and selecting the MCA allowed amount for SOC items. The structure records the selected value, category, and provenance fields indicating the contributing source(s), and may include flags when caps are enforced.

Flag unmatched 326 handles sponsor items that remain unresolved after matching. Before flagging, the engine executes a permutation-based re-tokenization pass that expands abbreviations and reorders multi-segment phrases, then re-embeds and re-queries the index. Items still unresolved are flagged with their top candidate explanations and scores. A secondary check can apply an auxiliary classifier to predict a likely code family and billing category and provide a suggested resolution with calibrated confidence for operator review.

Write audit record 328 generates a per-item record containing: the snapshot identifier and hash; model and dictionary versions; compact vector fingerprints; candidate lists; component scores and weights; the acceptance threshold in force; matching decisions; and policy rationales, including any cap enforcement. A deterministic run identifier ties all audit entries for a given execution to an exact configuration, enabling replay and verification within numerical tolerances.

Transmit payload 330 concludes the process by returning a machine-readable payload through the interface. The payload includes, for each reconciled set, the resolved procedure name, standardized procedure code, resolved billing category, selected cost value, contributing sources, and an audit reference. Flagged items are emitted with top candidate explanations and suggested next actions. In some embodiments, the system also produces a forecast dataset and associated cost projections for planning, which may be exported separately.

Forecast Dataset and Predictive Modeling for Budget Negotiations.

The system generates a forecast dataset after reconciliation by aggregating, per site and per procedure code family, the selected cost value, composite match score components, historical dispersion of site pricing, billing category, coverage determinations, and trial context features such as visit counts and frequency. Features include: code-match indicator, cosine similarity, numeric proximity term, billing-consistency indicator, code family, site region, payer mix proxy, historical selected cost mean and variance, and temporal markers for Medicare schedule year. The target variable is the observed selected cost value for completed reconciliations.

A regression model is trained to predict expected site costs for future trial schedules. Implementations include gradient-boosted trees or a neural network with categorical embeddings for code families and sites. Training uses a time-based split, early stopping, and monotonicity constraints when applicable to maintain clinical plausibility. Evaluation reports mean absolute percentage error and pinball loss for cost quantiles that are used to form negotiation ranges. The forecast service produces estimates and confidence intervals for planned procedures and writes the forecast bundle to the API so that sponsors can simulate alternate schedules.

Forecasts are produced under guardrails that include time-based train/validation splits, monotonic constraints where clinically appropriate, and drift monitoring against a fixed benchmark set. The forecast bundle records feature schemas and version identifiers so that downstream consumers can reproduce estimates and confidence intervals for a given reconciliation identifier.

Glossary of Claim Terms

Application programming interface (API) means the set of authenticated endpoints and schemas through which the reconciliation engine receives source datasets and returns machine-readable results. In the claimed method, the API is the conduit for: receiving the plurality of procedural items from the sponsor budget source, the Medicare Coverage Analysis source, and the site charge master source; returning a reconciled budget data structure; and transmitting audit records. A submission endpoint accepts a request body that serializes each item's procedure name, standardized procedure code, cost value, billing category, and optional frequency. Headers carry an idempotency key so identical submissions within a retention window return the prior response without reprocessing. All connections use Transport Layer Security and signed tokens identifying the caller. A status endpoint exposes the reconciliation identifier and phase transitions through ingestion, normalization, vectorization, candidate retrieval, scoring, matching, policy resolution, and payload assembly. A results endpoint emits a JSON document containing, for each reconciled set, fields for the resolved procedure name, resolved standardized procedure code, resolved billing category, selected cost value, contributing sources, an audit record reference, and the deterministic run identifier. A separate audit endpoint authorizes access to per-item audit records that include the composite match score components, weights used, vector fingerprints, code-family gating decisions, rule rationales, and any secondary classifier outputs. Version headers pin the model, calibration, and synonym-dictionary revisions used for a given run to ensure exact reproducibility from the audit trail.

Approximate nearest neighbor index means the in-memory data structure that stores unit-length embeddings and supports sublinear retrieval of top-k candidates for a sponsor item. In embodiments aligned with the claims, the index is a graph-based navigable small-world structure with a bounded maximum node degree and a configurable search-effort parameter that limits expansions per query. Site charge master embeddings are inserted into the index as nodes that maintain links to proximate neighbors in embedding space. Querying proceeds by greedy advancement with backtracking from an entry point to a local neighborhood that yields high-recall candidate sets at much lower cost than exhaustive comparisons. The index exposes operations for incremental insertion of new site items without requiring a full rebuild, and a maintenance task periodically rebalances links to preserve target recall and latency profiles. The claimed system queries this index for each sponsor item to obtain a ranked candidate set by cosine similarity, then computes a composite match score using code and billing signals. The index thus serves as a performance-critical primitive that enables sublinear candidate discovery, which the claims recite as "constructing . . . an approximate nearest neighbor index" and "querying the index to retrieve a ranked set of candidate site items." The index parameters, together with the embedding dimensionality and normalization rules, are stored with model metadata and recorded in audit for deterministic replays.

Audit report means the structured, append-only record set that documents, for every processed item, the data versions, intermediate computations, and decision rationales sufficient to reproduce outcomes. In the claimed method, an audit record includes: the ingestion snapshot identifier and cryptographic hash; the deterministic run identifier; model and calibration versions; the normalized texts; compact vector fingerprints for the embeddings; the top-k candidate list returned by the approximate nearest neighbor index; the composite match score for each candidate broken down into code-match, textual similarity, numeric proximity, and billing-consistency components; the acceptance threshold used; any code-family gating applied during Medicare Coverage Analysis alignment; the final match or flag outcome; the selected edge and weight in the maximum-weight matching; the resolved billing category and selected cost value; and the policy rule identifiers that produced those resolutions. The report further stores secondary-check predictions with confidence values when an auxiliary classifier is invoked. Audit records are digitally signed and written to append-only storage so that a replay utility can re-execute scoring, matching, and rule evaluation under the recorded versions to confirm equivalence within numerical tolerances. The API exposes an endpoint that returns audit entries for authorized clients by audit record reference. These artifacts satisfy the claims' requirements to "write an audit record" and enable regulatory validation, contract dispute resolution, and internal quality control.

Billing category means the classification applied to a procedural item that directs financial treatment during reconciliation and downstream invoicing. In the claims and embodiments, categories include research billable, standard of care billable, invoiceable, and non-billable. The billing category participates in the composite match score through a billing-consistency indicator that rewards compatible sponsor and site categories under stored policy rules. It also governs cost selection in the rule engine: for research billable items, the engine prefers the site cost unless constrained by a contract cap; for standard of care items, the engine selects the Medicare Coverage Analysis allowed amount where available; for invoiceable items, the engine preserves invoice routing while validating amounts against negotiated terms or institutional schedules; for non-billable items, the engine assigns a zero selected cost and records provenance indicating sponsor designation. When the sponsor and Medicare Coverage Analysis disagree, a priorities table may favor Medicare Coverage Analysis determinations for specific code families while retaining sponsor intent elsewhere. The billing category is stored for each source item at ingestion, is carried through normalization, and appears in the reconciled budget output as the resolved category with a pointer to the rule rationale. This term is thus directly implicated by claim elements that compute the composite score, apply policy rules, and emit resolved fields in the machine-readable payload.

Calibrated threshold means the acceptance value for the composite match score that determines whether a candidate pair proceeds to matching. Consistent with the claims, the threshold is derived offline by sweeping candidate values over a held-out validation set of historical reconciliations and measuring precision, recall, and false positive rate. An operator or automated procedure selects the value that satisfies target performance criteria, then stores the chosen threshold with the weight vector, embedding model identifier, and configuration checksum as model metadata. During live reconciliation, the scoring component reads this metadata and applies the same threshold to each candidate pair's composite score. The threshold ensures consistent behavior across runs and prevents drift caused by incidental model updates. Threshold revisions are versioned, audited, and included in the deterministic run identifier so that any prior decision can be replayed exactly. In certain embodiments, thresholds may be stratified by code family or by procedure class to account for heterogeneous risks of false matches, though each stratified value is still selected through the same validation process. The calibrated threshold thus operationalizes the claims' requirement to "determine that a candidate pair satisfies a similarity threshold" and anchors the system's precision-recall tradeoff in measurable, reproducible criteria.

Code family means a stored grouping of standardized procedure codes that share hierarchy or clinical equivalence and that the reconciliation engine treats as related for gating, normalization, and audit purposes. In the claimed flow, code families are used in at least three places. First, normalization maps raw codes to canonical families so that near-equivalent codes align consistently across sources. Second, Medicare Coverage Analysis influence on the composite score is gated so that a Medicare Coverage Analysis item can adjust a sponsor-site pair only if its code belongs to the same family as either the sponsor code or the site code. This prevents unrelated Medicare Coverage Analysis codes from biasing a match. Third, policy rules can be scoped by family, for example to prefer Medicare Coverage Analysis billing category determinations for imaging families while honoring sponsor designations for site-specific clinical services. The family taxonomy is versioned, stored with the synonym dictionary, and recorded in audit. Updates may incorporate externally published hierarchies and institution-specific mappings validated during prior reconciliations. Code families therefore provide a principled bridge between strict code equality and looser semantic similarity, and they satisfy the claim limitation that the Medicare Coverage Analysis item "is required to share a code family" before influencing the score.

Code match indicator means the binary variable that equals 1 when standardized procedure codes for a sponsor item and a candidate site item are exactly equal after normalization, and equals 0 otherwise. In the composite match score recited in the claims, this indicator is multiplied by a code weight that is configured to exceed other component weights. The effect is that exact code equality dominates the score whenever present, which accords with billing practice and reduces the risk of conflating clinically distinct procedures that happen to be textually similar. The indicator is computed after code cleaning, which includes stripping punctuation, harmonizing padding, and mapping legacy variants to canonical forms. The audit record shows the raw codes, the normalized codes, the indicator value, and the weight magnitude used at the time of the run. When Medicare Coverage Analysis alignment is attempted for a matched sponsor-site pair, a separate indicator reflects equality between the Medicare Coverage Analysis code and either the sponsor or site code. That second indicator contributes a predetermined score adjustment if and only if code-family gating permits. The code match indicator thus provides a crisp, reproducible signal in the scoring step claimed as "computing a composite match score that includes a code-match indicator."

Composite match score means the weighted sum used to evaluate candidate pairs and decide whether they satisfy the similarity threshold. The claimed score combines: a code-match indicator that rewards exact standardized procedure code equality; a cosine similarity term computed between unit-length embeddings of normalized procedure names and associated numeric features; a numeric proximity term that decays with the absolute difference between sponsor and site cost values according to a tunable scale; and a billing-consistency term that equals 1 when billing categories are compatible under stored policy rules. The weight vector is stored in configuration and constrained so that the code-match weight exceeds every other component weight, ensuring code equality dominates when present. The engine computes the score for each of the top-k candidates returned by the approximate nearest neighbor index. Pairs whose scores meet or exceed the calibrated threshold are eligible edges in the weighted bipartite graph used for maximum-weight matching. The audit record preserves every component value and the final sum so that decisions can be traced and replayed. The composite match score is thus the central quantitative mechanism that operationalizes the claim limitations calling for weighted aggregation of code equality, textual similarity, numeric proximity, and billing consistency.

Control vector means a fixed reference embedding, derived from a curated procedural description or canonical example, used in some embodiments to assess contextual similarity or to stabilize score calibration. While the independent claim resolves similarity through pairwise cosine values and a composite score, a control vector can serve two claim-consistent roles. First, during training and calibration, it provides a stationary point to monitor embedding drift and to scale numeric proximity terms so that the score distribution remains stable across model versions. Second, during secondary checks, it allows the system to detect items that deviate significantly from expected context within a code family and to route those items to manual review with an explicit "out-of-context" rationale. The control vector is produced by the same text-embedding function used for item embeddings and is stored alongside model metadata. Its identifier appears in audit when it influences acceptance thresholds or triggers context-based flags. Although optional, the concept aligns with the claims' emphasis on reproducible, parameterized similarity computations and on auditability of decision criteria.

Deterministic run identifier means the unique identifier computed for each reconciliation execution from the cryptographic hash of the ingestion snapshot and the version identifiers of all model and configuration artifacts used, including the embedding model, synonym dictionary, calibration weights and threshold, code-family taxonomy, and index parameters. The identifier is recorded in every audit record and is returned in the API responses so that any reported result can be tied to exactly one reproducible environment. A replay tool accepts the run identifier, fetches the recorded versions, and re-executes normalization, embedding, candidate retrieval, scoring, matching, and rule evaluation. Any divergence beyond stored numerical tolerances is reported with the step that produced it. The run identifier also enables durable referencing of results in downstream systems, such as contract management and invoicing, and supports change-control by making it obvious when a later model or policy change would have altered a past outcome. This construct implements the claims' requirement for tamper resistance and traceability of reconciliations that are transmitted via the API.

Dictionary of procedural terms and codes means the curated and continuously updated repository that maps abbreviations, synonyms, and variant phrasings to normalized tokens and links legacy or institution-specific codes to canonical standardized codes or code families. In the claims, the dictionary is used during normalization to expand abbreviations, lower-case and strip punctuation, and to map codes to canonical families before embedding. The dictionary also grows through the active learning loop: when a user resolves a flagged item, the confirmed equivalence of normalized texts is stored as a synonym pair and can be used to fine-tune the text-embedding function. Entries carry provenance, including who added them and from which reconciliation feedback they were derived, and are versioned so that a specific reconciliation run references a specific dictionary revision. The dictionary is a key input to the text-embedding function and to the permutation-based re-tokenization pass that generates alternative normalized texts for otherwise unmatched items. Its role is explicitly coupled to claim elements for normalization, caching of embeddings for repeated normalized texts, and ongoing model retraining.

Forecast dataset means the structured collection of features and labels aggregated from reconciled outputs and used to train a predictive model that estimates expected site costs for future trial schedules. Features include composite score components, resolved standardized procedure codes, code family identifiers, selected cost values, resolved billing categories, site region and type, contract cap occurrences, and trial context attributes such as visit counts or frequency. Labels may be realized costs observed post-reconciliation or adjudicated negotiated amounts. The dataset is time-stamped and versioned, enabling backtesting of predictive performance under different model releases. The claimed method references using reconciled items and their similarity scores to train a model that outputs expected site costs, which assists sponsors in planning budgets and evaluating the impact of adding or removing procedures. The forecast dataset is generated only after audit-complete reconciliations so that training does not ingest unreviewed or erroneous labels. Dataset construction records the deterministic run identifiers that contributed examples, allowing end-to-end traceability from prediction back to the reconciled items and their audit trails. This term therefore supports the claims' final limitation concerning generation of a forecast dataset and model training for budget negotiation support.

Historical clinical trial budgets means the corpus of prior sponsor budgets, Medicare Coverage Analyses, and site charge masters, together with their reconciled outcomes and audit trails, that the system uses for training and calibration.

In the claims, this dataset provides labeled positive and negative pairs for contrastive learning of the text-embedding function, hard negative mining for difficult near-matches, and held-out validation for threshold calibration. Each record includes normalized texts, standardized procedure codes, resolved billing categories, selected cost values, and code family identifiers. The corpus also supplies frequency statistics and cost distributions that inform numeric proximity scaling and policy defaults. Access to historical budgets is governed by data governance controls and de-identification rules so that protected information does not leak into embeddings or labels. Model versioning links trained artifacts back to specific subsets of this dataset, which is essential for reproducibility and for auditing the provenance of learned behavior. Historical clinical trial budgets therefore ground the machine-learning life cycle, directly satisfying claim elements that reference training on historical data and validating thresholds on held-out reconciliations.

Machine-learning model means the computational component that converts normalized texts and selected numeric features into fixed-length embeddings used for similarity computations, as well as auxiliary classifiers used for secondary checks. In one embodiment aligning with the claims, the primary model is a dual-encoder text embedding function trained with supervised contrastive learning on labeled pairs from historical reconciliations, with hard negatives retrieved by nearest-neighbor search under earlier checkpoints. Inputs are tokenized with a versioned vocabulary that knows clinical abbreviations and common budget phrasing. Numeric attributes, such as cost value and frequency, are scaled and concatenated or projected and added to the text vector. All embeddings are L2-normalized to unit length so that cosine similarity equals the dot product. Training uses an adaptive optimizer and early stopping based on validation loss. The model registry records artifact checksums, training set identifiers, and calibration metadata. Auxiliary models may predict a likely code family or billing category during the secondary check for flagged items. The claimed method explicitly recites training, caching, and hardware acceleration of vector computations, all of which are part of this term. In certain embodiments the text-embedding function is instantiated using openly available transformer checkpoints (for example, BERT, ROBERTa, or Sentence-BERT variants) fine-tuned on labeled reconciliation pairs. The system remains model-agnostic: any encoder capable of producing fixed-length, L2-normalized vectors from normalized procedure names (optionally fused with numerical attributes) may be substituted without departing from the described operation.

Maximum weight matching means the selection of a set of non-overlapping sponsor-to-site pairs that maximizes the sum of composite match scores subject to one-to-one constraints. The claims instantiate this step after candidate scoring by "forming a weighted bipartite graph" with sponsor items on the left, site items on the right, and edges only for pairs that satisfy the calibrated threshold, with edge weights equal to composite scores. In a typical implementation, the Hungarian algorithm operates on a finite cost matrix derived from the negated edge weights, assigning infinite cost to prohibited pairs so they cannot be chosen. Ties are broken deterministically using a stable key such as ingestion timestamp and normalized name order so that repeated runs under the same versions yield identical assignments. The selected matching prevents a single site item from being matched to multiple sponsor items, which could otherwise inflate totals or mask inconsistencies. The audit record stores the chosen edges and their weights, enabling inspection of alternatives that were close in score but excluded by the one-to-one constraint. Maximum weight matching thus enforces the structural limitation recited in the claims and contributes to reproducible, financially consistent reconciliation.

Medicare Coverage Analysis (MCA) means the dataset that specifies which clinical trial costs may be billed to Medicare and which are the sponsor's responsibility, along with allowed amounts and billing categories. In the claimed method, the Medicare Coverage Analysis is one of the three source inputs ingested into an immutable snapshot, and it participates in two core operations. First, a Medicare Coverage Analysis item can be aligned to a sponsor-site pair via exact code equality or a similarity search over embeddings, subject to the requirement that the Medicare Coverage Analysis code share a code family with either the sponsor or site code before it can influence the pair's composite score. Second, policy rules preferentially select the Medicare Coverage Analysis allowed amount as the selected cost value for items resolved to the standard of care billing category. The Medicare Coverage Analysis also serves as a reference for billing category conflicts and may override sponsor designations for certain families per stored priorities. All Medicare Coverage Analysis references, including code-family gating decisions and allowed-amount selections, are recorded in audit. This term thus directly supports claims requiring ingestion from Medicare Coverage Analysis sources and integration during scoring and policy resolution.

Medicare reimbursement means the payment amounts recognized by Medicare for covered services performed during clinical trials and the associated coverage determinations. Within the claimed system, Medicare reimbursement data appears within the Medicare Coverage Analysis input and is used by the policy rule engine to select the selected cost value for items resolved to the standard of care category. When the Medicare Coverage Analysis expresses a range or setting-dependent amounts, the engine selects the appropriate allowed amount for the trial's clinical context according to stored coverage guidelines. Medicare reimbursement values also serve as guardrails during numeric proximity scoring to prevent implausible sponsor-site price disparities from unduly increasing or decreasing similarity. The audit record stores the chosen Medicare reimbursement figure and the rule that referenced it, which supports post-hoc validation. Medicare reimbursement does not itself drive the approximate nearest neighbor candidate retrieval or textual similarity, but it materially affects the cost selection and therefore the reconciled budget output that the API returns. This term is therefore coupled to the claims' policy-resolution and output-generation elements.

Navigable small world graph means the proximity graph structure used to implement the approximate nearest neighbor index referenced in the claims. Nodes store unit-length embeddings for site charge master items. Edges connect nodes that are near neighbors under cosine distance. The graph is organized in layers that enable greedy search with backtracking to quickly traverse from an entry node to regions where high-similarity candidates reside. Two configuration parameters govern performance and memory: a maximum node degree that bounds how many neighbor links each node maintains, and a search-effort parameter that limits how many node expansions occur per query. Insertions add nodes and adjust neighbor lists with local rewiring to preserve navigability. Rebalancing tasks can prune or augment connections to maintain desired average degree. This structure yields high recall while avoiding the O(n) cost of exhaustive comparisons. In the claimed method, the graph enables "constructing" an index and "querying" it to retrieve candidates for scoring, thereby reducing latency and compute load on the matching and policy stages. Graph parameters and versions are persisted and included in audit and in the deterministic run identifier.

Negotiated terms means the contractually agreed rates, caps, and fee structures between the sponsor and a site that affect how costs are selected for research billable and invoiceable items. In the claimed policy rule engine, negotiated terms specify absolute caps, percentage caps over reference rates, site-specific premiums, or bundled fees that supersede default selections. When a negotiated cap is enforced, the engine records a cap-enforcement flag, the triggering reference (such as a Medicare Coverage Analysis allowed amount or a sponsor maximum), and the pre-cap computed value. Negotiated terms may also enumerate fee schedules for start-up, pharmacy handling, or data management that are treated as invoiceable and routed accordingly. Contract versions are time-stamped so the rule engine can use the correct schedule for the ingestion snapshot date. The reconciled output includes provenance indicating that a selected cost derives from a negotiated term rather than from a site charge master or Medicare Coverage Analysis amount. These mechanisms tie directly to the claim elements where the rule engine selects a selected cost value subject to contract caps and where provenance fields identify the source of the selected amount.

Numerical attributes means non-text features carried by each procedural item and consumed by the scoring and embedding stages of the claimed method. Representative attributes include cost value, frequency, overhead allocations, and optionally site-specific modifiers such as facility and professional split indicators. In one implementation consistent with the claims, scaled numeric features are concatenated or projected and then combined with the text embedding before L2 normalization so that the vector encodes both semantic and numerical context. Separately, the composite match score includes a numeric-proximity term computed as an exponential decay function of the absolute cost difference divided by a tunable scale parameter stored in configuration. The system calibrates that scale on held-out reconciliations to maintain target false positive and true positive rates. Numerical attributes do not replace the code-match indicator that dominates when standardized codes are equal. Instead, they supply complementary signal when codes differ or are absent. During policy resolution, numerical attributes also participate in rule evaluation, for example by comparing a site cost to a Medicare Coverage Analysis allowed amount or by applying negotiated caps. All uses are logged in the audit record so that downstream systems can trace how numeric values influenced the outcome.

Permutation based re-tokenization means generation of alternate normalized texts for an unmatched item, followed by re-embedding and re-querying the index as recited in the claims. The engine first expands abbreviations using the stored synonym dictionary, then produces constrained permutations that reorder multi-segment phrases, move modifiers such as "with contrast," and harmonize punctuation. Each variant passes through the same pipeline used for primary text: tokenize, normalize, embed to unit length, query the navigable small world index, and compute the composite match score against returned candidates. A variant budget limits the number of alternatives to preserve latency guarantees. If any variant satisfies the calibrated similarity threshold, the system promotes that match and records the exact normalization and permutation that led to acceptance. If no variant qualifies, the sponsor item is flagged for manual review with the top candidate explanations and scores so an operator can decide whether to expand the synonym dictionary or add a code mapping. This mechanism is a concrete text-processing improvement that reduces false negatives arising from word-order and abbreviation differences and directly implements the claim step that repeats retrieval and scoring for alternative tokenizations before flagging.

Permutation comparison means the evaluation procedure the engine uses when no direct CPT equality and no high textual similarity are present, where the system synthesizes and tests multiple term permutations across sources to locate a semantically aligned candidate. Unlike permutation based re-tokenization, which generates variants for a single unmatched item, permutation comparison coordinates variants across sponsor, site, and Medicare Coverage Analysis descriptions. The engine constructs a small cross-product of plausible rewrites using dictionary expansions, synonym swaps, and head-modifier reorderings, then computes embeddings for each element and performs top-k retrievals against the index. The composite match score is computed for each tested pair and the best-scoring pair is advanced to code-family gating and policy resolution if the score meets the calibrated threshold. The process is bounded by a variant budget and a time budget to ensure predictable runtime. Outcomes and tried variants are recorded in the audit record so the replay utility can reconstruct why a candidate was accepted or flagged. This definition ties directly to the claim elements that perform "permutation based re-tokenization," compute composite scores, apply a similarity threshold, and then flag unresolved items with explanations.

Policy rule set means the machine-readable collection of condition-action rules that the rule engine executes to select a cost, resolve a billing category, enforce caps, and record the rationale for each reconciled set as recited in the claims. Rules reference facts extracted during matching, such as standardized procedure code, code family, cosine similarity, numeric proximity, and billing categories from each source. Additional facts include negotiated terms, Medicare Coverage Analysis allowances, and trial context like visit number or inpatient versus outpatient setting. Example rules include: if billing category resolves to research billable and a negotiated cap exists, then select min (site cost, cap) and mark cap enforcement; if billing category resolves to standard of care and a Medicare Coverage Analysis allowed amount exists, then select that allowed amount; if sponsor and Medicare Coverage Analysis disagree on billing category within a sensitive code family, prefer Medicare Coverage Analysis. The rule set is versioned and bound to the reconciliation snapshot so that decisions are reproducible. Each rule execution emits a rule identifier and input facts into the audit record. The policy rule set operates after the maximum-weight matching step and implements the claim requirement to update the reconciled budget data structure with a selected cost value and resolved billing category.

Predictive model for expected site costs means a supervised regression model trained on a forecast dataset assembled from past reconciled outputs and trial context, used to estimate likely site costs for planned procedures and schedules as recited in the dependent claims. Features include code family identifiers, composite match-score components, historical selected cost values by site and region, billing category distributions, and visit-level factors such as frequency and inpatient status. Labels are realized selected costs from prior reconciliations under the applicable policy at the time of those runs. In one embodiment, the model outputs point estimates and confidence intervals for each planned item. Confidence intervals can be produced via quantile regression or by conformal post-processing on top of a base regressor. The system may aggregate item-level forecasts across a trial calendar to generate per-site and per-trial projections that inform negotiation. Predictions are not used to override the reconciliation of actual items. They are used upstream to propose budget targets and downstream to detect outliers during validation. Model artifacts are versioned and their use is recorded in the audit trail whenever forecasts influence an exported planning dataset.

Procedure code means a standardized alphanumeric identifier associated with a medical service and used in the claimed method both as a high-precision alignment signal and as a policy key. Examples include CPT, HCPCS, or institutionally normalized variants that can be mapped to a canonical namespace. During matching, the code-match indicator equals 1 when two items share identical standardized procedure codes and equals 0 otherwise. The composite match score assigns the code-match indicator a greater weight than any other term so that exact code equality dominates when present, as specified by the claims. Codes also seed code-family assignment, which gates whether a Medicare Coverage Analysis alignment can contribute score and determines which policy rules apply during cost selection. The ingestion pipeline validates codes against a schema and quarantines malformed entries to avoid polluting the index. When a human resolves a flagged item by asserting code equivalence, the dictionary of procedural terms and codes is updated so that future runs can recognize the mapping. All code usages and any cap enforcement tied to a code are recorded in the audit record linked to the ingestion snapshot.

Procedure name means the normalized textual description of a medical procedure used to compute embeddings for similarity search in the claimed method. Normalization includes tokenization, lowercasing, punctuation removal, expansion of common abbreviations, and application of synonym mappings from the dictionary of procedural terms and codes. The resulting normalized text is fed to the embedding function to produce a unit-length vector that captures semantic characteristics. Because sponsor, site, and Medicare Coverage Analysis sources can use different phrasing, procedure names serve as the primary vehicle for semantic alignment when codes differ or are absent. The engine stores the pre- and post-normalization forms so that the audit report can show exactly how text was transformed before embedding and retrieval. When an operator accepts or corrects a suggested match, the system can add a synonym pair to the dictionary so that subsequent runs embed equivalent names into nearby points in the vector space. Procedure names do not determine the final cost. They drive candidate retrieval and the cosine-similarity term in the composite match score that precedes policy resolution as recited in the claims.

Procedural data means the structured record for a single clinical procedure that the system processes during reconciliation. Each record includes at least procedure name, standardized procedure code, cost value, and billing category, as claimed. Optional fields can include frequency, facility and professional split flags, and provenance metadata like source identifier and ingestion timestamp. During ingestion, records are validated and transformed into a common internal schema so that downstream components can operate uniformly across CSV, Excel, JSON, and XML sources. The vectorization service reads procedure name and numerical attributes to compute an embedding and inserts the resulting vector into the index when the item is a site entry. Sponsor and Medicare Coverage Analysis items use the index for retrieval. Procedural data also feeds the composite match-score computation, the maximum-weight matching stage, and the policy rule engine that selects the cost and billing category for the reconciled budget data structure. All intermediate and final decisions that touch a given record are written to the audit report so that a complete, item-level lineage exists for regulatory review and replay.

Reconciled budget means the structured output that consolidates matched items across sources and records a selected cost value, a resolved billing category, and provenance for each matched set, as recited in the independent claim. In one embodiment the reconciled budget is a machine-readable JSON document keyed by a stable identifier per matched set and containing fields for resolved procedure name, standardized procedure code, selected cost, resolved billing category, contributing sources, and references to audit records. The selected cost equals the maximum permitted value under the active policy rule set, taking into account Medicare Coverage Analysis allowances and negotiated caps. For sponsor items that remain unmatched after maximum-weight matching and permutation-based re-tokenization, the reconciled budget contains flag entries with top candidate explanations, score components, and recommended next actions. Version fields bind the output to the ingestion snapshot, the embedding model, the synonym dictionary, and calibration parameters, which ensures deterministic replay. Because this output is consumed by a budget management system through an API, it also includes an export timestamp and an idempotency key so that downstream systems can process responses safely.

Rule engine means the software component that evaluates the policy rule set against matched items to determine the selected cost value and resolved billing category, enforce caps, and write rationale into the audit report, as required by the claims. The engine operates after the maximum-weight matching stage. Inputs include matched sponsor and site records, an optional aligned Medicare Coverage Analysis record, composite score components, code family assignment, and contextual metadata such as site, visit number, and inpatient status. Rules are expressed as condition-action statements with priorities and conflict-resolution behavior. The engine executes rules deterministically under the run's snapshot token, recording each fired rule's identifier and the facts used. If a rule depends on a negotiated cap, the engine computes the effective cap value, applies it, and sets a cap-enforcement flag. If billing categories conflict across sources, the engine consults a priorities table that is part of the rule set and records the basis for the final decision. The engine outputs the reconciled budget entries and appends rule rationales to the corresponding audit records so that decisions are explainable and reproducible.

Secondary check means the post-matching validation step applied to items that remain flagged after the claimed retrieval, scoring, and permutation procedures. In one embodiment the system invokes an auxiliary classifier that predicts a likely code family and a likely billing category from normalized text and numerical attributes. The classifier can be a transformer fine-tuned for classification with cross-entropy loss over code-family labels and billing labels. The secondary check does not silently override acceptance thresholds or the maximum-weight matching decision. Instead, it produces a suggested resolution and a calibrated confidence score that are written into the audit record and surfaced in the budget management system for user review. If a user accepts the suggestion, the system updates the dictionary of procedural terms and codes, expands the synonym mappings, and schedules fine-tuning of the embedding model with the new positive or negative pair so that similar items are handled automatically in future runs. The secondary check therefore reduces manual workload while preserving the deterministic reconciliation behavior required by the claims.

Semantic characteristics means the linguistic and contextual features of a procedural description that determine its position in the embedding space used by the claimed system. Examples include head nouns and modifiers, modality markers such as "with contrast," anatomical terms, and common synonyms. During normalization the engine preserves medically salient tokens and expands abbreviations so that embeddings reflect meaning rather than formatting artifacts. The embedding function, which can be a dual encoder trained via contrastive learning, maps tokens and their local context into a fixed-length unit vector. Cosine similarity between two such vectors approximates semantic relatedness and forms the textual component of the composite match score. By representing semantics numerically, the system can compare descriptions that differ in word order or phrasing and still retrieve high-quality candidates from the index. Semantic characteristics are learned from labeled pairs and hard negatives mined from prior reconciliations, which positions semantically equivalent descriptions near each other. The audit record stores a compact vector fingerprint so that the semantic contribution to a decision can be verified later without exposing full vectors.

Site charge master means the institution-specific catalog of billable services and associated prices that serves as one of the three primary data sources in the claimed method. Each entry typically includes a procedure name or internal descriptor, a standardized procedure code or local code mapped to a canonical code, a site-specific cost value, and a billing category designation. During ingestion, site charge-master items are normalized and inserted into the approximate nearest-neighbor index as nodes. When sponsor items are processed, the engine queries this index to retrieve candidate site items by cosine similarity, then computes composite match scores and participates in maximum-weight matching to create one-to-one sponsor-site assignments. The selected site cost may be chosen by the rule engine when the resolved billing category is research billable, subject to negotiated caps, and the source of the selected cost is recorded in the reconciled budget's provenance fields. Site charge-master updates trigger incremental index maintenance so that the search space reflects current site pricing without full rebuilds. Site catalogs are bound to the ingestion snapshot to ensure reproducible runs.

Sponsor's budget means the sponsor-provided list of planned research procedures and associated financial terms that supplies one of the three primary inputs to the claimed reconciliation pipeline. Each sponsor item includes a procedure name, a standardized procedure code when available, a proposed cost value or fee schedule, and a billing category designation. The ingestion controller validates and normalizes these records, then stores them in the staging table keyed by a stable internal identifier. During processing, each sponsor item is embedded and used to query the site index to obtain a ranked candidate list. The composite match score is computed for each candidate pair, followed by the maximum-weight matching step that enforces a one-to-one assignment. The sponsor record then participates in Medicare Coverage Analysis alignment and policy resolution. If the billing category resolves to research billable, the rule engine may prefer the site cost subject to caps. If unresolved after permutation procedures, the sponsor item is flagged with candidate explanations. The sponsor's budget therefore drives the per-item reconciliation loop and anchors the reconciled budget entries exported through the API.

Transformation results means the machine-readable set of fields that describe how the claimed system transformed inputs into reconciled outputs for each item or matched set. Representative fields include the normalized texts used for embedding, the embedding model version, the top-k candidate list with cosine similarities, the composite match-score components and weights, the acceptance threshold used, the maximum-weight matching decision and competing edges, and the selected cost with policy rule rationale. Transformation results are emitted both in the audit report and, in summarized form, in the API payload returned to the budget management system. They enable downstream consumers to understand why a particular match was accepted or rejected, what influence code equality and numeric proximity had, and how caps or Medicare Coverage Analysis allowances affected cost selection. Because each reconciliation run is bound to an ingestion snapshot and deterministic run identifier, transformation results can be used by a replay utility to verify that re-executing the pipeline with the recorded versions reproduces the same outputs within numerical tolerance as required by the claims.

Transformer-based model means a neural network that uses self-attention to encode token sequences and that the claimed system employs for contextual understanding in difficult matching scenarios and for auxiliary classification during secondary checks. In one embodiment, a dual-encoder architecture is fine-tuned via supervised contrastive learning so that semantically equivalent procedure names map to nearby vectors. Hard negatives are mined by nearest-neighbor retrieval against a checkpoint and used to sharpen decision boundaries. Tokenization rules align with the normalization pipeline so that medically salient subtokens are preserved. Training uses de-identified, curated pairs derived from historical reconciliations, with early stopping on a validation set and model registry packaging of tokenizer rules, calibration parameters, and checksums. The model's outputs are used in two ways within the claimed method: first, to produce fixed-length unit-norm embeddings that feed the approximate nearest-neighbor index and composite score; second, to classify likely code families or billing categories for flagged items during the secondary check. Model version identifiers are recorded in audit records to ensure explainability and reproducibility.

Unified output format means the schema that the claimed system uses to serialize the reconciled budget and associated audit references for delivery through the API. In one embodiment the format is JSON and contains, per matched set, fields for resolved procedure name, standardized procedure code, resolved billing category, selected cost value, contributing sources, and an audit record reference. For flagged items the payload includes the top candidate explanations, component scores, and suggested next actions. Envelope fields include a reconciliation identifier, an idempotency key, the ingestion snapshot identifier, and version identifiers for the embedding model, synonym dictionary, calibration weights, and index configuration. This structure enables consistent downstream ingestion by budget management systems and supports idempotent retries. Because the format includes provenance and rule rationale pointers, recipients can later retrieve detailed audit records to verify policy application and matching decisions. The unified output format does not change the matching decision. It carries the specific fields that satisfy the claim requirement to transmit a machine-readable payload that captures outcomes and enables financial and regulatory processing.

Vector-based similarity algorithm means the computational method that evaluates semantic relatedness between two normalized textual descriptions by operating on their unit-length embeddings. In one embodiment aligned with the claims, cosine similarity is computed as the inner product of the sponsor vector and the site vector, yielding a value in the range [0, 1] for non-negative embeddings. Because vectors are L2-normalized, the dot product equals cosine similarity, which reduces computation to a single fused multiply-add loop that benefits from hardware acceleration. The similarity value becomes the text component of the composite match score, which also includes a code-match indicator, a numeric proximity term, and a billing consistency term. The algorithm is used both during approximate nearest-neighbor retrieval to rank candidates and during final scoring to determine whether a candidate pair satisfies the calibrated acceptance threshold. Parameters and implementation details, including precision, tolerance, and accelerator kernels, are versioned and recorded so that identical inputs reproduce identical similarity values during replay.

Vector fingerprint means a compact, stable representation of a unit-length embedding that the system records in audit trails to enable later verification without exposing full floating-point vectors. In one embodiment a locality-sensitive hash or a quantized binary code is computed from the normalized vector by projecting onto a small set of random or learned hyperplanes and storing the resulting bit string. The fingerprint is deterministic given the model version and projection basis recorded in the audit record. During replay or audit, the system can recompute embeddings for the same normalized text under the same model version, derive the fingerprint, and verify that it matches the stored value. Fingerprints allow auditors to confirm that the same vector was used to compute cosine similarities and composite scores while avoiding disclosure of the exact numeric representation. The audit record stores fingerprints for sponsor, site, and Medicare Coverage Analysis embeddings used in accepted matches and for top candidates associated with flagged items, providing a privacy-preserving but verifiable linkage to the vector computations recited in the claims.

Vector representations means fixed-length numerical encodings of normalized procedure names, optionally augmented with projected numerical attributes, that the claimed system uses for similarity search and scoring. Embeddings are produced by the trained text-embedding function, then L2-normalized to unit length so that cosine similarity reduces to a dot product. Dimensions can be 256 or 384 elements in one implementation that balances accuracy and throughput. Embeddings for site items are inserted into the navigable small world index. Embeddings for sponsor and Medicare Coverage Analysis items are used to query the index and to compute composite match scores with retrieved candidates. Cache entries store embeddings for frequent normalized phrases and abbreviations keyed by the model version so that a model upgrade invalidates incompatible vectors. Hardware acceleration can execute embedding computations and dot products when available, with numeric tolerances recorded to ensure replay equivalence. By transforming free-form text into vectors, the system implements a concrete improvement in how a computer processes heterogeneous budget records and satisfies the claim steps that depend on vector generation and similarity evaluation.

Weighted bipartite graph means the graph the system constructs to enforce a one-to-one assignment between sponsor items and site items after candidate scoring, as recited in the claims. Left nodes correspond to sponsor items. Right nodes correspond to site items. Edges exist only for pairs whose composite match score meets or exceeds the calibrated threshold. Edge weights equal the composite match score. The engine computes a maximum-weight matching to select a set of non-overlapping edges that maximizes total confidence across all assignments. In one embodiment the matching is computed by the Hungarian algorithm over a dense score matrix derived from candidate pairs, with infinite cost assigned to disallowed pairs. Deterministic tie-breaking uses a stable key that combines ingestion timestamp, source identifiers, and lexical order of normalized names so that identical inputs yield identical matchings. The selected edges drive subsequent Medicare Coverage Analysis alignment and policy resolution, while unmatched sponsor items flow to permutation procedures and possible flagging. The graph and matching decisions are recorded in the audit report for replay.

Weighted values means the configuration parameters that determine how the composite match score balances code equality, textual similarity, numeric proximity, and billing consistency as specified in the claims. The weight vector W includes at least a code-match weight, a text weight, a numeric weight, and a billing-consistency weight. The configuration constrains the code-match weight to exceed each other component so that exact code equality dominates when present. Weights are calibrated offline using a held-out validation set of historical reconciliations to achieve target precision and recall while maintaining a bound on false positives. The calibrated weights, together with the acceptance threshold and model identifier, are stored in model metadata and bound to the run's snapshot token so that scoring decisions are reproducible. During runtime, the engine computes the composite score for each candidate pair using the stored weights and accepts the pair if the score meets or exceeds the calibrated threshold. The audit record stores the component scores and the weight vector used so that reviewers can reconstruct how each factor contributed to acceptance or flagging.

Technical Effects and Improvements to Computer Function

The system described herein produces concrete improvements in computer operation for heterogeneous budget data. Normalization and unit-length embeddings transform free-form text into numeric vectors that can be compared with constant-time inner products. The navigable small-world index yields sublinear candidate retrieval and reduces the number of vector comparisons required per sponsor item. The calibrated composite score with code-dominant weighting systematically integrates code equality, textual similarity, numeric proximity, and billing consistency, which reduces false matches that would arise from any single signal. Weighted bipartite matching enforces one-to-one assignments and removes duplication that would otherwise inflate totals. Snapshotting and versioned models make reconciliation runs deterministic, replayable, and auditable. These techniques, taken together, enable fast, accurate, and reproducible reconciliation at scales and speeds that manual methods or naive string matching cannot achieve. The improvements arise from specific data structures and algorithmic steps that enhance the way a computer processes and reconciles budget records, not from automating a business practice using a generic computer.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

What is claimed is:

1. A computer-implemented method executed by one or more processors for automated reconciliation of clinical trial budgets, the method comprising:

a. receiving, from each of a sponsor budget source, a Medicare Coverage Analysis source, and a site charge master source, a plurality of procedural items, each item including a procedure name, a standardized procedure code, a cost value, and a billing category;

b. normalizing the procedure names by tokenizing text, lowercasing, removing punctuation, expanding abbreviations using a stored synonym dictionary, and mapping procedure codes to canonical code families;

c. generating, for each procedural item, a fixed-length vector embedding that encodes the normalized procedure name and the numerical attributes of the item by applying a trained text-embedding function and then normalizing each vector to unit length;

d. constructing in memory an approximate nearest neighbor index over vectors of items from the site charge master source, the index being graph-based and parameterized to bound search fan-out and to provide sub-linear retrieval of candidate neighbors;

e. for each item from the sponsor budget source, querying the index to retrieve a ranked set of candidate site items by cosine similarity of the corresponding vectors;

f. computing, for each candidate pair, a composite match score that includes a code-match indicator, a cosine similarity term, a numeric similarity term based on the difference between cost values, and a billing-consistency term derived from the billing categories, each term weighted according to a stored configuration, and determining that a candidate pair satisfies a similarity threshold when the composite match score meets or exceeds a calibrated threshold;

g. forming a weighted bipartite graph whose left nodes correspond to items from the sponsor budget source and whose right nodes correspond to items from the site charge master source, whose edges connect pairs that satisfy the similarity threshold, and whose edge weights equal the composite match scores;

h. selecting a one-to-one assignment between sponsor items and site items by computing a maximum-weight matching over the weighted bipartite graph;

i. for each matched pair, identifying a corresponding item in the Medicare Coverage Analysis source by either exact standardized procedure code equality or by applying the steps of elements (c) through (f) with the Medicare Coverage Analysis source serving as a comparison dataset, and adjusting the composite match score with a predetermined code-match weight when the Medicare Coverage Analysis code equals the sponsor code or the site code;

j. updating a reconciled budget data structure in memory that stores, for each matched set of items across sources, a selected cost value equal to a maximum permitted value determined by a policy rule set that enforces Medicare Coverage Analysis allowances and contract caps, and that stores a resolved billing category determined by a rule engine, and that stores provenance fields identifying the source of the selected cost value;

k. flagging as unresolved any sponsor budget item that remains unmatched after the maximum-weight matching and a permutation-based re-tokenization pass that reorders tokens and expands abbreviations, and storing for each flagged item the top candidate explanations and scores;

l. Writing an audit record for each processed item that includes a vector fingerprint, the candidate list, the composite match score components and weights, a match or flag outcome, and the rule rationale applied during cost and billing resolution; and m. transmitting the reconciled budget data structure and the audit records as a machine-readable payload through an application programming interface to a budget management system.

2. The method of claim 1, wherein the text-embedding function is trained by contrastive learning on labeled pairs of matching and non-matching procedural items derived from historical clinical trial budgets and where hard negative examples are mined by nearest-neighbor retrieval during training.

3. The method of claim 1, wherein the approximate neighbor index is a navigable small-world graph index configured with a maximum node degree and a search effort parameter that limit the number of visited nodes per query.

4. The method of claim 1, wherein the one-to-one assignment is computed by executing a Hungarian algorithm over a cost matrix derived from the composite match scores.

5. The method of claim 1, wherein the numeric similarity term is computed as an exponential function of an absolute difference between cost values divided by a tunable scale parameter stored in configuration.

6. The method of claim 1, wherein the similarity threshold is calibrated by evaluating a held-out validation set of historical budgets to achieve a target false positive rate and target true positive rate and storing the calibrated threshold in model metadata.

7. The method of claim 1, further comprising taking an immutable snapshot of the three sources at an ingestion timestamp and executing all steps against the snapshot to produce a reproducible reconciled budget and audit trail.

8. The method of claim 1, further comprising caching vector embeddings for previously seen procedure names in a key-addressable store and reusing cached vectors when the same normalized text appears in subsequent reconciliations.

9. The method of claim 1, further comprising performing incremental insertion of new site charge master items into the approximate nearest neighbor index without full rebuild of the index.

10. The method of claim 1, wherein the code-match indicator receives a higher weight than the cosine similarity term such that exact standardized procedure code equality dominates the composite match score when present.

11. The method of claim 1, wherein the permutation-based re-tokenization pass generates alternative token orders and abbreviation expansions for an unmatched sponsor item and repeats elements (c) through (f) for each alternative until either the similarity threshold is satisfied or the item is flagged.

12. The method of claim 1, wherein the rule engine selects the cost value as the site cost value when the billing category is research billable and as the Medicare Coverage Analysis allowed amount when the billing category is standard of care, subject to contract caps, and records any cap enforcement in the audit record.

13. The method of claim 1, further comprising performing a secondary check on each flagged item by applying a trained auxiliary classifier that predicts a likely code family and a likely billing category and providing a suggested resolution with a confidence score in the audit record.

14. The method of claim 1, wherein the synonym dictionary is automatically expanded when a user resolves a flagged item, by storing the normalized text of the resolved items as a synonym pair and retraining the text-embedding function on the updated dictionary.

15. The method of claim 1, wherein the audit record includes a cryptographic hash of the ingestion snapshot and a deterministic run identifier to ensure tamper resistance and traceability.

16. The method of claim 1, wherein the machine-readable payload is a JSON document that includes, for each reconciled item, fields for resolved procedure name, resolved standardized procedure code, resolved billing category, selected cost value, the contributing sources, and the audit record reference.

17. The method of claim 1, further comprising executing vector computations on a hardware accelerator when available and falling back to a processor implementation when the accelerator is not available, while producing numerically equivalent results within a stored tolerance.

18. The method of claim 1, wherein the approximate nearest neighbor query returns a fixed top-k candidate list per sponsor item and the composite match score is computed only for the returned candidates.

19. The method of claim 1, wherein the Medicare Coverage Analysis item selected in element (i) is required to share a code family with either the sponsor code or the site code before it can influence the composite match score.

20. The method of claim 1, further comprising generating a forecast dataset that aggregates composite match scores and selected cost values across reconciled items and training a predictive model that outputs expected site costs for a future trial schedule to inform budget negotiations.

\* \* \* \* \*